United States Patent
Kato et al.

(10) Patent No.: US 10,835,895 B2
(45) Date of Patent: Nov. 17, 2020

(54) COMPOUND AND SYNTHESIS METHOD THEREFOR

(71) Applicant: The University of Tokyo, Tokyo (JP)

(72) Inventors: Takashi Kato, Tokyo (JP); Ken Kawata, Tokyo (JP)

(73) Assignee: THE UNIVERSITY OF TOKYO, Tokyo (JP)

(\*) Notice: Subject to any disclaimer, the term of this patent is extended or adjusted under 35 U.S.C. 154(b) by 9 days.

(21) Appl. No.: 16/090,405

(22) PCT Filed: Mar. 30, 2017

(86) PCT No.: PCT/JP2017/013404
§ 371 (c)(1),
(2) Date: Oct. 1, 2018

(87) PCT Pub. No.: WO2017/170934
PCT Pub. Date: Oct. 5, 2017

(65) Prior Publication Data
US 2019/0111418 A1    Apr. 18, 2019

(30) Foreign Application Priority Data

Apr. 1, 2016   (JP) .................................. 2016-073976

(51) Int. Cl.
| | |
|---|---|
| B01J 39/07 | (2017.01) |
| C07F 1/02 | (2006.01) |
| C08F 36/16 | (2006.01) |
| C02F 101/20 | (2006.01) |
| C02F 1/42 | (2006.01) |
| B01J 39/20 | (2006.01) |
| C07C 49/825 | (2006.01) |
| C07F 9/6568 | (2006.01) |
| C07C 269/02 | (2006.01) |
| C07C 67/343 | (2006.01) |
| C07F 9/53 | (2006.01) |
| C08L 101/00 | (2006.01) |
| C07C 45/68 | (2006.01) |
| C08F 236/04 | (2006.01) |
| C07C 49/92 | (2006.01) |
| C07C 69/716 | (2006.01) |
| B01J 20/26 | (2006.01) |
| C08K 5/51 | (2006.01) |
| C08F 22/20 | (2006.01) |
| C07F 1/00 | (2006.01) |
| C02F 1/68 | (2006.01) |
| C07C 269/06 | (2006.01) |
| B01J 20/22 | (2006.01) |
| C07C 271/48 | (2006.01) |
| C08K 5/00 | (2006.01) |

(Continued)

(52) U.S. Cl.
CPC ............. *B01J 39/20* (2013.01); *B01J 20/223* (2013.01); *B01J 20/261* (2013.01); *B01J 39/07* (2017.01); *C02F 1/42* (2013.01); *C02F 1/683* (2013.01); *C07C 45/68* (2013.01); *C07C 49/825* (2013.01); *C07C 49/92* (2013.01); *C07C 67/343* (2013.01); *C07C 69/716* (2013.01); *C07C 269/02* (2013.01); *C07C 269/06* (2013.01); *C07C 271/48* (2013.01); *C07F 1/005* (2013.01); *C07F 1/02* (2013.01); *C07F 9/5304* (2013.01); *C07F 9/5325* (2013.01); *C07F 9/5329* (2013.01); *C07F 9/65685* (2013.01); *C08F 22/20* (2013.01); *C08F 36/16* (2013.01); *C08F 236/045* (2013.01); *C08K 5/0091* (2013.01); *C08K 5/51* (2013.01); *C08L 101/00* (2013.01); *C02F 2101/10* (2013.01); *C02F 2101/20* (2013.01); *C02F 2103/08* (2013.01)

(58) Field of Classification Search
CPC combination set(s) only.
See application file for complete search history.

(56) References Cited

U.S. PATENT DOCUMENTS 3,405,163 A \* 10/1968 Bambury et al. ..... C07C 69/716
560/51
4,500,601 A    2/1985 Whitcomb
(Continued)

FOREIGN PATENT DOCUMENTS

JP   59-31768 A      2/1984
JP   10228638 A  \*  8/1998
(Continued)

OTHER PUBLICATIONS

Machine translation of JP 10-228638 A, retrieved Feb. 2020 (Year: 2020).\*

(Continued)

*Primary Examiner* — Nicole M. Buie-Hatcher
(74) *Attorney, Agent, or Firm* — Knobbe, Martens, Olson & Bear, LLP

(57) ABSTRACT

An acetylacetone derivative is useful for capturing a metal element by complexation. A convenient and very versatile synthesis method can be used to synthesize the derivative. The derivative can have the following formula:

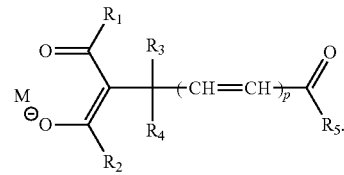

16 Claims, 4 Drawing Sheets

(51) Int. Cl.
    *C02F 103/08*    (2006.01)
    *C02F 101/10*    (2006.01)

(56) References Cited

U.S. PATENT DOCUMENTS

| | | | |
|---|---|---|---|
| 4,894,384 A | 1/1990 | Cecere et al. | |
| 4,943,673 A * | 7/1990 | Norman | C07C 45/45 585/843 |

FOREIGN PATENT DOCUMENTS

| | | | | |
|---|---|---|---|---|
| JP | 11-001625 A | 1/1999 | | |
| JP | H 11-199855 A | 7/1999 | | |
| JP | 2002-138069 A | 5/2002 | | |
| JP | 2014-504632 A | 2/2014 | | |
| JP | 5565377 B2 | 8/2014 | | |
| WO | WO-2005075601 A1 * | 8/2005 | ......... | H01L 51/0087 |
| WO | WO-2005124889 A1 * | 12/2005 | ............ | H05B 33/14 |
| WO | WO 2011/111607 A1 | 9/2011 | | |
| WO | WO-2015119268 A1 * | 8/2015 | ............ | C07C 49/92 |

OTHER PUBLICATIONS

Kostyuk et al., "Anodic Oxidation of Gadolinium Metal in Presence of Thenoyltrifluoroacetone", 2006, 79(1), 74-78 (Year: 2006).*

Shaabani et al. "1,4-Diionic organophosphorous compounds: Stereoselective synthesis of dialkyl 2-(1,1,1,5,5,5-hexafluoro-2,4-dioxo-pentane-3-yl-3-yide)-3-triphenylphosphinoiobutane-1,4-dioates", Journal of Fluorine Chemistry, 2000, 103, 155-157 (Year: 2000).*

Healy, T.V., Synergism in the Solvent Extraction of Alkali Metal Ions by the Thenoyl Trifuloracetone, Journal of Inorganic and Nuclear Chemistry, vol. 30, pp. 1025-1036, 1968.

Ibata, T., et al., Reaction of diazo ketones in the presence of metal chelates Reaction with β-diketones, Chemistry Letters, vol. 11, pp. 1267-1270, 1976.

International Search Report, dated Jul. 18, 2017, in International Application No. JP/2017/013404.

Kumari, N., et al., Synthesis of some novel β-diketones and β-ketoesters of 4-methyl sulphonyl benzoyl methylene bromide, Chemical Science Transactions, vol. 2, No. 1, pp. 81-84, 2013.

Banerjee, D., et al, Recent Advances in s-Block Metal Carboxylate Networks, Crystal Growth & Design, vol. 11, pp. 4704-4720, 2011.

Baruah, J.B., et al., Copper(I) promoted allylic nucleophilic substitutions: a synthetic and mechanistic study, New Journal of Chemistry, vol. 18, pp. 961-971, 1994.

Carey, F.A., et al, Organic Chemistry, 9th Edition, McGraw-Hill, New York, pp. 833-840, 2014.

Fan, X., et al., Tandem reaction of 1,2-allenic ketone with α-halo ketone or α-halo ester in water: an efficient and sustainable synthesis of 1,3,4'-tricarbonyl compounds, Green Chemistry, vol. 13, pp. 3218-3223, 2011.

Healy, T.V., Synergism in the Solvent Extraction of Alkali Metal Ions by the Thenoyl Trifuloracetone, Journal of Inorganic and Nuclear Chemistry, vol. 30, pp. 1025-1306, 1968.

Kamata, I., et al., Li(I) Selective Resins Prepared by Mans of Molecular Imprinting Technique Utilizing Synergistic Effect, Bulletin of the Society of Sea Water Science, Japan, vol. 56, pp. 228-233, 2002.

Li, N-S., et al., Synthesis of 2-Acyl-1,4-1-8 diketones via the Diacylation of α,β-Unsaturated Ketones, Organometallics, vol. 17, pp. 3815-3818, 1998.

Liquid Crystal Handbook, 3.6 Metal complex liquid crystal, b. Coordination stereochemistry, edited by Liquid Crystal Handbook Editorial Board, Maruzen Co., Ltd., pp. 337-339, 2000.

Matano, Y., et al., Novel synthesis of alkylbismuthonium salts and their reaction with some nucleophiles. First x-ray structural analysis of a stabilized alkylbismuthonium tetrafluoroborate, Tetrahedron Letters, vol. 34, No. 52, pp. 8457-8460, 1993.

Meng, X., et al., Heterogeneous synthesis of 1,4-enediones and 1,4-diketones with manganese oxide molecular sieves OMS-2 as a recyclable catalyst, Catalysis Communications, vol. 69, pp. 239-242, 2015.

Stetter, H., et al., Addition of aldehydes to activated double bonds. XXV. Syntheses and reactions of branched tricarbonyl compounds, Chemische Berichte, vol. 114, pp. 564-580, 1981.

Thirumurugan, A., et al., Heterothallic Inorganic-Organic Frameworks of Sodium-Bismuth Benzedicrobxylates, Crystal Growth & Design, vol. 10, No. 4, pp. 1736-1741, 2010.

* cited by examiner

Schematic Diagram 1

1-position, 5-position substituent 3-position substituent

Element having an independent electron pair, and ability to stabilize metal element

COMPOUND AND SYNTHESIS METHOD THEREFOR

PRIORITY AND CROSS REFERENCE TO RELATED APPLICATIONS

This application is the U.S. National Phase Application under 35 U.S.C. § 371 of International Application No. PCT/JP2017/013404, filed Mar. 30, 2017, designating the U.S. and published as WO 2017/170934 A1 on Oct. 5, 2017, which claims the benefit of Japanese Application No. JP 2016-073976, filed Apr. 1, 2016. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present invention relates to an acetylacetone derivative which is useful for capturing a metal element by complexation, and a convenient and highly versatile synthesis method thereof. More particularly, the present invention relates to an acetylacetone derivative having a substituent at 3-position, and an acetylacetone derivative capable of forming a structure by a composition of a suitable ligand with the acetyl acetone group, and a synthesis method thereof.

BACKGROUND ART

An acetylacetone group is useful as a ligand of a light emitting material, due to high complexation performance with rare earth elements (Patent Literature 1). In addition, use as a water treatment agent for efficiently capturing various heavy metal elements even from a dilute dissolved state, using the high complexation performance has been suggested (Patent Literature 2). In particular, studies for efficiently capturing rare elements such as uranium or lithium dissolved in seawater have already begun in the 1960s, and particularly for lithium, it has been reported that a combination of acetylacetone and phosphine oxide is preferred (Non Patent Literature 1). In this century, it was reviewed to polymerize and solidify a commercially available acetylacetone derivative having a substituent at 1-position or 5-position and trioctylphosphine oxide by divinyl benzene (Non Patent Literature 2); however, since then no study reports using the acetylacetone derivative of this family have seen until recently.

As the acetylacetone derivative, those having a substituent such as a long chain alkyl group, an aromatic ring, or a heterocycle at 1-position or 5-position by Claisen condensation of two molecules of ester in the existence of a base are relatively conveniently available (Non Patent Literature 3). This has an active methylene moiety at 3-position and is condensed with an amino group or a carbonyl group therefrom to extend a conjugated system, thereby being useful as a precursor of a colorant or a dye. For this reason, there is no need to introduce a substituent at 3-position.

However, since it is preferred to form the metal salt of metal ions for efficiently capturing the metal ions from general waste water including seawater, it is required to have the lowest pKa possible. Appropriate pKa of acetylacetone is expected to be 3 to 6, considering the elution of captured metal by a hydrochloric acid solution, and in order to realize such low pKa, hexafluoro acetylacetone having closed 1,5-position is preferred, and thus, a convenient synthesis method of a compound having a side chain extended from only remaining 3-position is currently required. However, from the background of development of the above-described synthesis method, for the acetylacetone derivative having a side chain having a relatively long chain and a side chain having various functional groups introduced at 3-position, there are very few examples of the compound, and a convenient synthesis method thereof is hardly known.

CITATION LIST

Patent Literature

Patent Literature 1: WO2011111607 A1
Patent Literature 2: JP 5565377 B2

Non Patent Literature

Non Patent Literature 1: T. V. HEALY, Inorg, nucl. chem., 1968. Vol. 30, pp. 1025 to 1136.
Non Patent Literature 2: Ichiro Kamata, Kosuke Araki, Masahiro Goto, Akihiro Sakoguchi, Fumiyuki Nakashio, Shintaro Hurusaki, Bull. Soc. Sea Water Sci. Jpn., 56, 228-233 (2002).
Non Patent Literature 3: Carey, Francis A. (2006). Organic Chemistry (Sixth ed.). New York, N.Y. Exhibition McGraw-Hill.
Non Patent Literature 4: Liquid Crystal Handbook, 3.6 Metal complex liquid crystal, b. Coordination stereochemistry, page 339, edited by Liquid Crystal Handbook Editorial Board, Maruzen Co., Ltd., published in 2000
Non Patent Literature 5: Debasis Banerjee and John B. Parise, Crystal Growth & Design, Vol. 11, page 4704, 2011.
Non Patent Literature 6: A. Thirumurugan, Jin-Chong Tan, and Anthony K. Cheetham, Crystal Growth & Design, Vol. 10, No. 4, page 1736, 2010.

SUMMARY

An object of the present invention is to provide a convenient synthesis method of using an acetylacetone derivative having a simple structure and being relatively inexpensive as a starting material to introduce a versatile substituent at 3-position, and provide a functional element capable of capturing a metal element with high selectivity by the acetylacetone derivative substituted at 3-position.

The object of the present invention can be achieved by the following means.

[1] A compound represented by the following General Formula (1):

[Chem. 1]

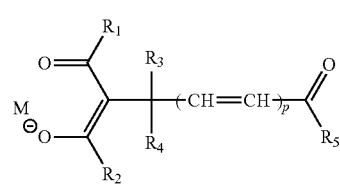

(1)

wherein

M is a hydrogen atom, or a monovalent or higher valent metal ion which may have a ligand;

$R_1$ and $R_2$ are, each independently, a substituted or unsubstituted alkyl group, alkenyl group, aryl group, or heterocyclic group, and these groups may include a polymerizable group;

$R_3$ and $R_4$ are, each independently, a hydrogen atom, a substituted or unsubstituted alkyl group, aryl group, or heterocyclic group, and these groups may include a polymerizable group;

$R_5$ is a substituted or unsubstituted alkyl group, alkenyl group, alkynyl group, aryl group, heterocyclic group, alkoxy group, aryloxy group, alkylamino group, or arylamino group, and these groups may include a polymerizable group;

each of $R_1$ to $R_5$ does not include the polymerizable group, or at least one of $R_1$ to $R_5$ includes the polymerizable group; and p is 1 or 0, with a proviso that when p=0, $R_5$ is not an alkoxy group having 4 or less carbon atoms.

[2] The compound according to [1], wherein at least one of $R_1$ and $R_2$ is a trifluoromethyl group.

[3] The compound according to [1] or [2], wherein $R_5$ includes the polymerizable group.

[4] The compound according to any one of [1] to [3], wherein $R_5$ includes a divalent residue represented by the following General Formula (2):

[Chem. 2]

wherein k is 2 or 3; and m is an integer of 1 to 20.

[5] The compound according to any one of [1] to [4] wherein M is a lithium ion.

[6] The compound according to any one of [1] to [5], wherein the compound represented by General Formula (1) has pKa of 3 to 6.

[7] The compound according to any one of [1] to [6], wherein the compound represented by General Formula (1) expresses liquid crystallinity.

[8] A composition including the compound according to any one of [1] to [7], wherein M is a monovalent or higher valent metal ion which may have a ligand.

[9] A polymer composition comprising a polymer including a compound represented by General Formula (1) as a structural unit, wherein said compound has a polymerizable group.

[10] The polymer composition according to [9], wherein in General Formula (1), M is a monovalent or higher valent metal ion which may have a ligand.

[11] The composition according to any one of [8] to [10], wherein the composition has a cumulative structure by self-organization.

[12] A composition comprising the compound according to any one of [1] to [7], and a compound represented by General Formula (3):

[Chem. 3]

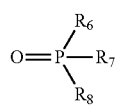

wherein
$R_6$, $R_7$, and $R_8$ are, each independently, a substituted or unsubstituted alkyl group, aryl group, or heterocyclic group, which may include a polymerizable group;

any two of $R_6$, $R_7$, and $R_8$ may form a 5 to 7-membered ring containing a phosphorus atom to which the two are bonded together; or a dimer may be formed through any one of $R_6$, $R_7$, and $R_8$; and each of $R_6$ to $R_8$ does not include a polymerizable group, or at least one of $R_6$ to $R_8$ includes a polymerizable group.

[13] The composition according to [12], wherein at least one of the compound represented by General Formula (1) and the compound represented by General Formula (3) includes the polymerizable group, and a polymer including the compound including the polymerizable group as a structural unit is included in the composition.

[14] The composition according to [12] or [13], wherein in General Formula (1), M is a monovalent or higher valent metal ion which may have a ligand.

[15] The composition according to any one of [12] to [14], wherein the composition has a cumulative structure by self-organization.

[16] A process for preparing a polymer composition, comprising: polymerizing a composition comprising a compound represented by General Formula (1) wherein M is a monovalent or higher valent metal ion which may have a ligand; and at least one of $R_1$ to $R_5$ includes a polymerizable group; eluting a metal salt thereof; and substituting M with a hydrogen atom.

[17] A process for preparing a polymer composition, comprising: polymerizing a composition comprising a compound represented by General Formula (1) wherein M is a monovalent or higher valent metal ion which may have a ligand, and a compound represented by General Formula (3), in which at least one of both compounds has a polymerizable group; eluting a metal salt thereof; and substituting M with a hydrogen atom.

[18] A method of selectively capturing a metal ion, using the polymer composition obtained by the process according to [16] or [17].

[19] A process for preparing a compound represented by General Formula (1), comprising reacting a compound represented by the following General Formula (4) and a compound represented by the following General Formula (5):

[Chem. 4]

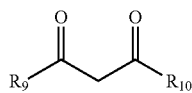

wherein $R_9$ and $R_{10}$ are a substituted or unsubstituted alkyl group, aryl group, or heterocyclic group, which may include a polymerizable group;

[Chem. 5]

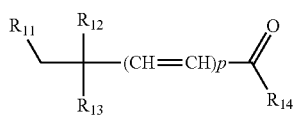

wherein $R_{11}$ is a halogen element; $R_{12}$ and $R_{13}$ are a hydrogen atom, a substituted or unsubstituted alkyl group, aryl group, or heterocyclic group; $R_{14}$ is a substituted or unsubstituted alkyl group, alkenyl group, alkynyl group, aryl group, heterocyclic group, alkoxy group, aryloxy group, alkylamino group, or arylamino group; groups defined as $R_{12}$ to $R_{14}$ may include a polymerizable group; and p is 0 or 1, with a proviso that when p=0, $R_{14}$ is not an alkoxy group having 4 or less carbon atoms.

[20] The process according to [19], wherein the compound represented by General Formula (4) and the compound represented by General Formula (5) are reacted in the coexistence of an iodine salt of an organic compound.

A convenient synthesis method of acetylacetone having a substituent at 3-position has not been known until now. One of the reasons is that the hydroxyl group produced by keto-enol tautomerism of an acetylacetone group has high reactivity, so that once substituted, it is very difficult to release the hydroxyl group under a mild condition, and it is also difficult to synthesize a compound having other functional groups together. The other reason is that an acetylacetone group having low pKa is needed for efficiently capturing a metal from a neutral solution, and one of the preferred structures is a hexafluoroacetylacetone group, however, expensive synthetic raw materials are used to stepwise synthesize the group, and it is considered that it is difficult to control the reaction. Accordingly, it is preferred to perform reaction with acetylacetone at the final stage; however, as a reagent which reacts with the acetylacetone under a mild condition, only benzyl halide is known. However, it was found that the condensate is also very thermally unstable depending on the substituents.

In contrast, in the present invention, an α-haloacetyl compound which is an active halogen compound and also preferred from the viewpoint of structural diversity is reacted with substituted acetylacetone under a relatively mild condition in one stage, thereby capable of easily obtaining the substituent at 3-position. The α-haloacetyl compound becomes the substituent at 3-position, and when the compound has an acetyl group disposed at the end of the side chain in the state that many functional groups, liquid crystal mesogen, or a polymerizable group is imparted as ketone, ester, and amide, and the end can be easily bromated to N-bromosuccinimide immediately before, and thus, the compound becomes a synthetically highly versatile synthetic intermediate.

In addition, it is possible that the acetylacetone derivative of the present invention which is characterized by being used alone or in combination with other ligands to have good complexation ability with various metal ions has various functional substituents disposed at 3-position, and when the substituent is a mesogen group in a straight chain form, the mesogen groups in which adjacent hydrophilic metal acetonate groups face each other are aligned on both sides on a straight line, whereby formation of a metal acetonate liquid crystal having a new regular tetrahedral structure which has never been reported (Non Patent Literature 4) is expected, and an industrial use value including expression of new complexation ability of the derivative is high.

DETAILED DESCRIPTION

Figure 1:
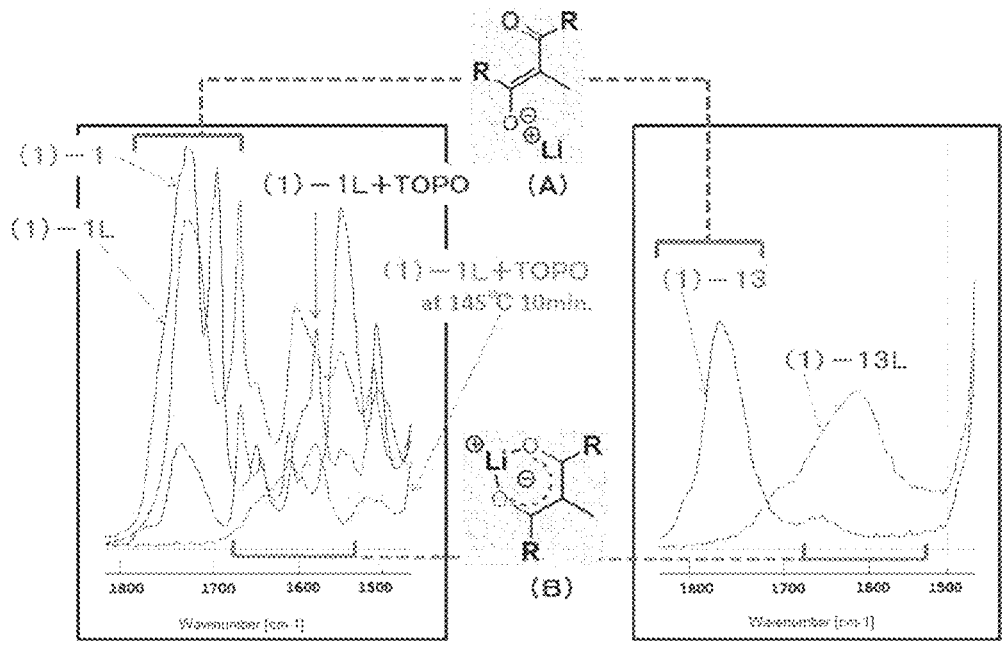
FIG. 1 is FT-IR spectra of (1)-1, (1)-1L, (1)-1L TOPO complex, (1)-1L TOPO complex (after heat treatment), (1)-13, and (1)-13L.
Figure 2:
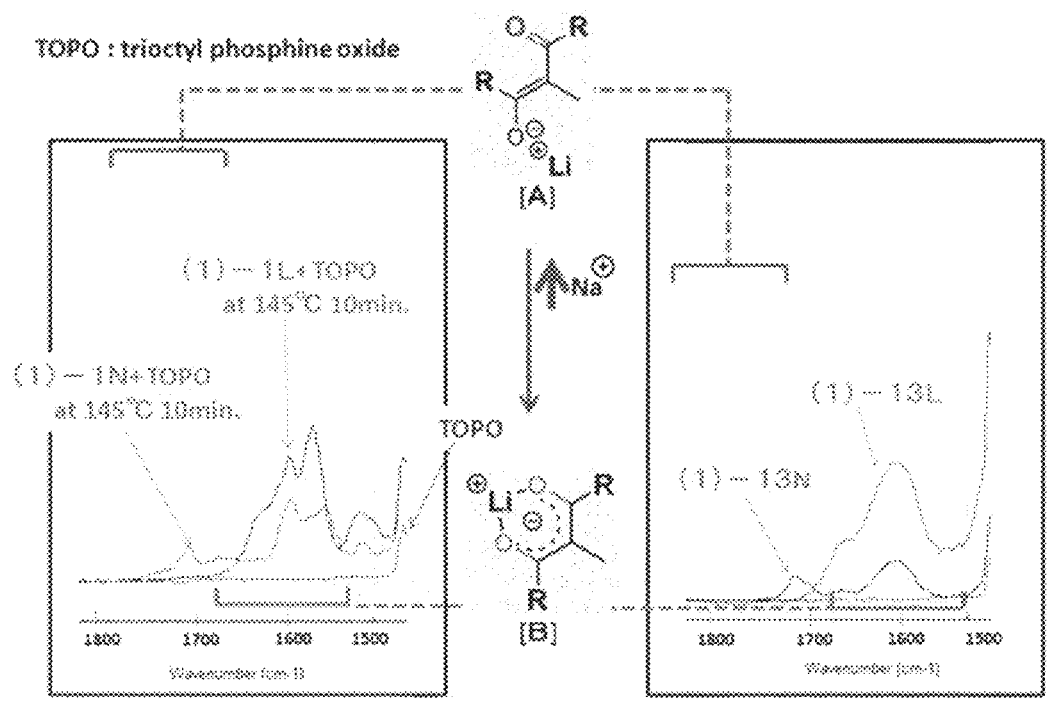
FIG. 2 is FT-IR spectra of (1)-1L TOPO complex, (1)-1N TOPO complex, (1)-13L, and (1)-13N.

Hereinafter, details of each component according to the present invention will be sequentially described.

One embodiment of the present invention is a compound represented by the following General Formula (1):

[Chem. 1]

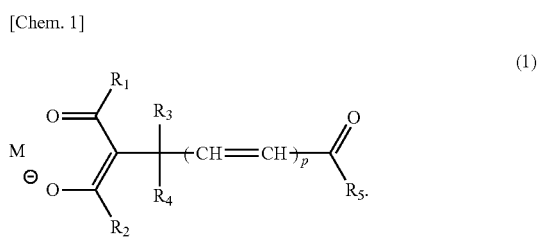

In General Formula (1), M is a hydrogen ion, or a monovalent or higher valent metal ion which may have ligand. Almost all metal ions correspond to so called acetylacetonate which is formed of a complex formed by acetylacetone and a metal ion. Therefore, though the acetylacetonate is not limited to any metal atoms as a preferred example, alkali metal ions, alkali earth metal ions, first to fourth transition metal ions, earth metal ions, and boron group ions are included.

Meanwhile, for one of the uses of the present invention of selectively capturing dissolved metals, rare metal element ions may be included as M, and for a function of a cumulative structural film to retain the metal, rare earth element ions used in light emitting materials, magnets, hydrogen occlusion alloy, and the like may be included. Specifically, ions such as platinum, palladium, indium, gallium, cesium, rubidium, molybdenum, vanadium, scandium, yttrium, uranium, and lithium may be included.

In addition, demand for lithium carbonate as a constituent component of a lithium ion secondary battery and the like, used for electric vehicles (EV) and the like is recently increasing, and for a use of selectively capturing a dissolved lithium ion from salt lake and the like, it is preferred that M is a lithium ion.

In General Formula (1), $R_1$ and $R_2$ are, each independently, a substituted or unsubstituted alkyl group, aryl group, heterocyclic group, alkenyl group, or alkynyl group, preferably a substituted or unsubstituted alkyl group, aryl group, or heterocyclic group.

The alkyl group includes a straight chain, branched, and cyclic alkyl groups, and the straight chain and branched alkyl groups may include, for example, a methyl group, an ethyl group, a propyl group, an isopropyl group, a tert-butyl group, a pentyl group, a hexyl group, a methoxyethoxyethyl group, and the like, and preferably a methyl group, a trifluoromethyl group, a perfluoroalkyl group, for example, a pentafluoroethyl group, a nonafluorobutyl group, a pentafluoroheptyl group, and the like. The cyclic alkyl group (cycloalkyl group) may include, for example, a cyclohexyl group, a cyclopentyl group, and the like.

The aryl group may include, for example, a phenyl group, a naphthyl group, an anthracenyl group, and the like.

The heterocyclic group may include, for example, a pyridyl group, a thiazolyl group, an oxazolyl group, an imidazolyl group, a furyl group, a thienyl group, a pyrrolyl group, a pyrazinyl group, a pyrimidinyl group, a pyridazinyl group, a selenazolyl group, a sulfonyl group, a piperidinyl group, a pyrazolyl group, a tetrazolyl group, and the like.

The alkenyl group may include, for example, an ethenyl group, a propenyl group, a buthenyl group, a cycloalkenyl group such as a cyclopropenyl group and a cyclohexenyl group, and the like, and the alkynyl group may include, for example, an ethynyl group, a propargyl group, and the like.

The alkyl group, the aryl group, the heterocyclic group, the alkenyl group, or the alkynyl group may be substituted, and the substituent thereof may include halogens (fluorine, chlorine, bromine, and iodine), alkoxy groups (e.g., a methoxy group, an ethoxy group, an ethoxyethoxy group, an ethoxydiethyleneoxy group), or amino groups (e.g., a methylamino group, a dimethylamino group, and a dimethylaminoethylamino group).

In addition, in the inside or at the end of the substituted or unsubstituted alkyl group, aryl group, heterocyclic group, alkenyl group, or alkynyl group, the following polymerizable group may be included.

$R_3$ and $R_4$ are, each independently, a hydrogen atom, a substituted or unsubstituted alkyl group, aryl group, or heterocyclic group, and the hydrogen atom is preferred. The substituted or unsubstituted alkyl group, aryl group, and heterocyclic group are as similarly described regarding $R_1$ and $R_2$.

$R_5$ is a substituted or unsubstituted alkyl group, alkenyl group, alkynyl group, aryl group, heterocyclic group, alkoxy group, aryloxy group, alkylamino group, arylamino group, alkylthio group, or arylthio group, and preferably a substituted or unsubstituted alkyl group, alkenyl group, alkynyl group, aryl group, heterocyclic group, alkoxy group, aryloxy group, alkylamino group, or arylamino group.

The substituted or unsubstituted alkyl group of $R_5$ may include, for example, a methyl group, an ethyl group, a propyl group, an isopropyl group, a tert-butyl group, a pentyl group, a hexyl group, an octadecyloxyethyl group, a heptadecyloxymethyl group, an acryloyloxymethyl group, an acryloyloxyethylaminocarbonyloxypropyl group, a glycidyloxymethyl group, a hexadecyloxytetraethyleneoxymethyl group, a hexadecadienyloxytetraethyleneoxymethyl group, and the like.

The substituted or unsubstituted alkenyl group may include, for example, an ethenyl group, a propenyl group, and the like.

The substituted or unsubstituted alkynyl group may include, for example, an ethynyl group, a propargyl group, and the like.

The substituted or unsubstituted aryl group may include, for example, a phenyl group, a methoxyphenyl group, an octyloxyphenyl group, an acryloyloxyphenyl group, a glycidyloxyphenyl group, an acryloyloxyethylaminocarbonyloxyphenyl group, a hexadecyloxytetraethyleneoxyphenyl group, a hexadecadienyloxytetraethyleneoxyphenyl group, and the like.

The substituted or unsubstituted heterocyclic group may include a pyridyl group, a thiazolyl group, an oxazolyl group, an imidazolyl group, a benzothiazolyl group, a benzoxazolyl group, a benzimidazolyl group, a furyl group, a pyrrolyl group, a pyrazinyl group, a pyrimidinyl group, a pyridazinyl group, a selenazolyl group, a sulfolanyl group, a piperidinyl group, a pyrazolyl group, a tetrazolyl group, a thiadiazolyl group, and the like.

The substituted or unsubstituted alkoxy group may include, for example, a methoxy group, an ethoxy group, a propyloxy group, a pentyloxy group, a cyclopentyloxy group, a hexyloxy group, a cyclohexyloxy group, a propenyloxy group, a propargyloxy group, an acryloyloxy group, an acryloyoxyethylaminocarbonyloxyethylamino group, a glycidyloxy group, an octadecyloxy group, a heptadecyloxy group, a hexadecyloxytetraethyleneoxy group, a hexadecadienyloxytetraethyleneoxy group, and the like.

The substituted or unsubstituted aryloxy group may include, for example, a phenoxy group and the like.

The substituted or unsubstituted alkylamino group may include, for example, a methylamio group, an ethylamino group, a propylamino group, a pentylamino group, a cyclopentylamino group, a hexylamino group, a cyclohexylamino group, a propenylamino group, a propargylamino group, an acryloylamino group, a glycidylamino group, an octadecylamino group, a heptadecylamino group, a hexadecyloxytriethylene oxyethylamino group, a hexadecadienyloxytriethylene oxyethylamino group, and the like.

The substituted or unsubstituted arylamino group may include, for example, a phenylamino group, a methoxyphenylamino group, a pentyloxy group, a cyclopentyloxyphenylamino group, a cyclohexyloxyphenylamino group, a propenyloxyphenylamino group, a propargyloxyphenylamino group, an acryloyloxyphenylamino group, a glycidyloxyphenylamino group, an octadecyloxyphenylamino group, a hexadecyloxytetraethylene oxyphenylamino group, a hexadecadienyloxytetraethylene oxyphenylamino group, and the like.

The substituted or unsubstituted alkylthio group may include, for example, a methylthio group, a hexadecylthio group, and the like, and the substituted or unsubstituted arylthio group may include, for example, a phenylthio group and the like.

In addition, in the inside or at the end of the substituted or unsubstituted alkyl group, alkenyl group, alkynyl group, aryl group, heterocyclic group, alkoxy group, aryloxy group, alkylamino group, arylamino group, alkylthio group, or arylthio group, a polymerizable group described below may be included.

In General Formula (1), each of $R_1$ to $R_5$ does not include the polymerizable group, or at least one of $R_1$ to $R_5$ includes the polymerizable group.

The polymerizable group may include an ethynyl group, a propargyl group, a vinyl group, an allyl group, a vinylphenyl group, an acryloyl group, a methacryloyl group, an epoxy group, a glycidyl group, a butanedienyl group, a sorbyl group, and the like. These polymerizable groups may not be included, but is included preferably in at least one of $R_1$ to $R_5$, more preferably in $R_5$, and still more preferably at the end of $R_5$.

In the case that $R_5$ includes the polymerizable group, a non-limited preferred example of the polymerizable group includes an acryloyl group, a methacryloyl group, a glycidyl group, a butanedienyl group, or a sorbyl group. A non-limited example of the compound having such $R_5$ is represented by the following (1)-1 to (1)-31.

In General Formula (1), p is 1 or 0. However, when p=0, $R_5$ is not an alkoxy group having 4 or less carbon atoms.

In one aspect of the compound represented by General Formula (1), it is preferred that at least one of $R_1$ and $R_2$ is a trifluoromethyl group, and it is more preferred that both of $R_1$ and $R_2$ are a trifluoromethyl group. The reason is that the acetylacetone group forming a metal salt is needed to be dissociated to form a metal salt, and for this, it is preferred that $R_1$ and $R_2$ are an electron withdrawing group. In addition, since brine, salt water, and waste water for generally capturing and recovering metals, including seawater are often close to neutrality, when the pKa of the composition including the compound of the present invention and the above compound is unduly low for eluting and recovering the captured metal salt, it is necessary to use a strong acid, and considering the repeat durability of the compound of the present invention, or the composition formed therefrom, pKa is often preferably 1 to 8, more preferably 2 to 7, and most preferably 3 to 6. However, when the metal is recovered from waste water having a special pH, it is preferred to select the compound of the present invention having a pKa corresponding to the special pH, of course. From this point also, it is preferred that both $R_1$ and $R_2$ are a trifluoromethyl group. In this case, the tetrafluoroacetylacetone of General Formula (4) forms a metal complex which is thermally stable and easily volatilized, with copper, palladium, platinum, and the like, and since it is used for CVD, tetrafluoroacetylacetone is a commercially available material, which is useful as a raw material of CVD.

In the compound of the present invention, it is important to have a long chain substituent at 3-position of the acetylacetone derivative. Although it is not intended to be bound to a theory, when the long chain substituent of the acetylacetone derivative forming a regular tetrahedral structure by complexation is at 1-position, 5-position, or both positions, as shown in the following Schematic Diagram 1, the substituent of the other ligand forming the regular tetrahedral structure is generally very likely to extend in a vertical direction with a long chain substituent of the acetylacetone derivative, and both of the substituents intersect with each other at the metal. Meanwhile, in the case of the acetylacetone derivative having a long chain substituent at 3-position, the substituent of the facing ligand is extended in an opposite direction to form a rod-like structure as a whole, and thus, it is expected that the acetylacetone derivative substituted at 3-position relatively easily forms a laminate structure or an anisotropic structure.

As such, it can be seen that the necessity of introducing a substituent at 3-position of the acetylacetone group is not derived from the conventional knowledge that the acetylacetone group easily captures a metal together with a ligand, but comes from an idea of cumulative structuring for actively imparting thermodynamic stability to a functional site of capturing a metal with the acetylacetone group.

In General Formula (1), each of $R_1$ to $R_5$ does not have the polymerizable group, or at least one of $R_1$ to $R_5$ includes the polymerizable group. The polymerizable group may include an ethynyl group, a propargyl group, a vinyl group, an allyl group, a vinylphenyl group, an acryloyl group, a methacryloyl group, epoxy group, glycidyl group, butanedienyl group, sorbyl group, and the like. These polymerizable groups may not be included, but included preferably in at least one of $R_1$ to $R_5$, more preferably in $R_5$, and still more preferably at the end of $R_5$.

In addition, when the polymerizable group is present at $R_5$ of General Formula (1), preferably at the end of $R_5$, there is little concern about an influence on the expression of liquid crystallinity expected when the acetylacetone group at the end of the molecule becomes the metal salt, and it is expected that the orientation of the acetylacetone derivative substituted at 3-position can be more mildly rapidly fixed.

In one aspect of the compound of the present invention, $R_5$ includes a divalent residue represented by the following General Formula (2). That is, in the inside of a substituted or unsubstituted alkyl group, alkenyl group, alkynyl group, aryl group, heterocyclic group, alkoxy group, aryloxy group, alkylamino group, arylamino group, alkylthio group, or arylthio group which is an option defined as $R_5$, the divalent residue represented by General Formula (2) is included.

[Chem. 2]

—{O(CH$_2$)k}m-    (2)

In Formula (2), k is 2 or 3, and preferably 2. m is an integer of 1 to 20, preferably 2 to 10, and more preferably 3 to 6.

A non-limited example of the case that $R_5$ includes the divalent residue represented by General Formula (2) includes an ethyleneoxy group, a diethyleneoxy group, a triethyleneoxy group, a tetraethyleneoxy group, a propyleneoxy group, a dipropyleneoxy group, a tripropyleneoxy group, a butyleneoxy group, and a dibutyleneoxy group. The polymer including these groups is preferred in terms of water permeability, and also expression of liquid crystallinity is expected with a combination thereof with a long chain alkyl group. In this respect, a triethyleneoxy group and a tetraethyleneoxy group are more preferred.

In one preferred aspect of the present invention, the compound represented by General Formula (1) basically has a rod-like structure, and has a possibility of expressing liquid crystallinity by selecting an appropriate functional group. This liquid crystal is described in the entire Non Patent Literature 4 in detail. In the intermediate state between crystal and liquid, liquid crystal refers to a state that some order in the direction of the particles is maintained, but an order in a three-dimensional position is lost. The liquid crystal is largely classified into a thermotropic liquid crystal and a lyotropic liquid crystal. The thermotropic liquid crystal undergoes phase change only by heat or pressure, but the lyotropic liquid crystal is composed of multiple components, thereby undergoing phase change by temperature and component configuration. A representative liquid crystal phase includes a nematic liquid crystal, a smectic liquid crystal, and the like. The nematic liquid crystal is a liquid crystal corresponding to the above-described anisotropic liquid. Since the nematic liquid crystal has no position regularity, it has fluidity similar to liquid. The smectic liquid crystal is a liquid crystal having one-dimensional centroid order, that is to say, having a layered structure. In addition, the smectic liquid crystal is classified into several phases again, from whether the molecule is tilted to the layer structure, what order each molecule has inside each layer, or the like.

The liquid crystal used in the present invention may be any one of the thermotropic liquid crystal, the lyotropic liquid crystal, the nematic liquid crystal, and the smectic liquid crystal. The merit of using the liquid crystal is that transporting and retaining of a metal ion, and substitution with a hydrogen ion are flexibly carried out, and at the same time, regular molecules, and furthermore various functional groups surround the metal ion with the same conformation, regardless of the presence or absence of the metal ion, and maintain the state, whereby selectivity of the metal ion is expected to be increased.

It is considered that it is more preferred that the compound represented by General Formula (1) expresses liquid crystallinity, in the case of using the compound as a material for recovering a metal salt, in particular a lithium salt.

Although it is not intended to be bound to a theory, since it is assumed that the operation that the composition comprising the compound of the present invention captures a metal salt from a liquid including the desired metal salt, and then elutes the metal salt is performed repeatedly, the composition is required to have durability against repeated expansion and contraction. Therefore, the composition is stable when capturing the metal salt in a rigid crystal body or a metal organic structure which is a metal organic framework (MOF), however, in a thermodynamically unstable state when eluting the metal salt, so that the metal ion is substituted with the hydrogen atom, and the repeat durability is problematic. In addition, for both capturing and eluting, a large amount of metal ions is needed to move in the composition at a high speed, and in the vicinity of a metal ion capturing site, a site which is path of the metal ion is needed, and structural flexibility is required. In this regard, it is preferred that the compound of the present invention expresses liquid crystallinity, since the compound has flexibility and uniform processability.

Another merit of liquid crystallinity is that a regular structure such as a crystal is cumulated. For example, a lithium salt is known to be stabilized in the regular tetrahedral structure, in which a distance between a lithium ion and an oxygen atom is 2.0 Å (Non Patent Literature 5), and by incorporating the salt in the liquid crystal, the cumulative structure may be further stabilized in a position relation capable of forming a regular tetrahedral structure having a constant size. Incidentally, in the case of the regular tetrahedral structure by sodium, a distance between a sodium ion and an oxygen atom is 2.4±0.2 Å (Non Patent Literature 6), and it can be seen that there is a considerable difference. Therefore, the lithium salt of the compound of the present invention, preferably the organization structure of the lithium salt representing the liquid crystal structure, is fixed by polymerization, and it is expected that the composition obtained by eluting a lithium ion from the polymer composition easily captures the lithium ion more selectively than the sodium ion.

In the compound of the present invention, by substituting a liquid crystalline mesogen group at 3-position, it is possible to achieve higher density by a self-organizing structure.

Another embodiment of the present invention is a composition comprising a compound wherein in General Formula (1), M is a monovalent or higher valent metal ion which may have a ligand.

Another embodiment of the present invention is a polymer composition in which the compound represented by General Formula (1) has a polymerizable group, and is polymerized by the polymerizable group, thereby forming a polymer composition including a polymer including the compound as a structural unit (repeating unit).

In a preferred aspect of the polymer composition, the compound represented by General Formula (1) includes a monovalent or higher valent metal ion which may have a ligand as M. Almost all metal ions correspond to so called acetylacetonate which is formed of a complex formed by acetylacetone and a metal ion. Therefore, though the acetylacetonate is not limited to any ions of metal atoms as a preferred example, alkali metal ions, alkali earth metal ions, first to fourth transition metal ions, earth metal ions, and boron group ions are included.

Meanwhile, for one of the uses of the present invention of selectively capturing dissolved metals, rare metal element ions may be included, and specifically, ions such as platinum, palladium, indium, gallium, cesium, rubidium, molybdenum, vanadium, scandium, yttrium, uranium, and lithium may be included.

In addition, demand for lithium carbonate as a constituent component of a lithium ion secondary battery and the like, used for electric vehicles (EV) and the like is recently increasing, and for a use of selectively capturing a dissolved lithium ion from salt lake and the like, it is preferred that M is a lithium ion.

The composition or the polymer composition preferably has a cumulative structure by self-organization.

Another embodiment of the present invention is a composition comprising the compound represented by General Formula (1), and a compound represented by the following General Formula (3).

[Chem. 3]

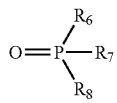

(3)

In Formula (3), $R_6$, $R_7$, and $R_8$ are, each independently, a substituted or unsubstituted alkyl group, aryl group, or heterocyclic group, which may include the polymerizable group as described above regarding $R_5$.

Here, any two of $R_6$, $R_7$, and $R_8$ may form a 5 to 7-membered ring containing a phosphorus atom to which the two are bonded together.

In addition, a dimer may be formed through any one of $R_6$, $R_7$, and $R_8$.

Each of $R_6$ to $R_8$ does not include the polymerizable group, or at least one of $R_6$ to $R_8$ includes the polymerizable group.

The substituted or unsubstituted alkyl group, aryl group, and heterocyclic group are as similarly described regarding $R_1$ and $R_2$.

The 5 to 7-membered ring containing a phosphorus atom to which any two of $R_6$, $R_7$, and $R_8$ are bonded together may further contain a N, O, or S atom. In addition, the 5 to 7-membered ring may contain an unsaturated bonding or have a substituent. The substituent may include halogen (fluorine, chlorine, bromine, and iodine), an alkoxy group (e.g., a methoxy group, an ethoxy group, an ethoxyethoxy group, an ethoxydiethyleneoxy group), and an amino group (e.g., a methylamino group, a dimethylamino group, and a dimethylaminoethylamino group).

A dimer may be formed through any one of $R_6$, $R_7$, and $R_8$. Such a compound may include, for example, a dimer formed through alkyl (a methylene group, an ethylene group, and the like) (compounds (3)-7 and (3)-8 as described below), a dimer formed through a benzene ring (compounds (3)-9 and (3)-10 as described below), and the like.

That is, it can be seen that the compound represented by General Formula (1) also forms a stable lithium salt with the phosphine oxide compound represented by General Formula (3). In this case, it is preferred that the phosphine oxide compound has twice the equivalent of the acetylacetone.

Therefore, one molecule of phosphine oxide compound in which the difunctional phosphine oxide group is substituted with a neighboring carbon atom is more preferred. $R_6$, $R_7$, and $R_8$ of General Formula (3) are a substituted or unsubstituted alkyl group, aryl group, or heterocyclic group, and each of $R_6$ to $R_8$ does not include the polymerizable group, or at least one of $R_6$ to $R_8$ includes the polymerizable group.

In a preferred aspect of the polymer composition, the compound represented by General Formula (1) includes a monovalent or higher valent metal ion which may have a ligand, as M.

Another embodiment of the present invention is a polymer composition in which at least one of the compound represented by General Formula (1) or the compound represented by General Formula (2) has a polymerizable group, the compound is polymerized by the polymerizable group, and a polymer including the compound as a structural unit (repeating unit) is included.

In a preferred aspect of the polymer composition, the compound represented by General Formula (1) includes a monovalent or higher valent metal ion which may have a ligand, as M.

The composition or polymer composition preferably has a cumulative structure by self-organization. For this reason, it is preferred that the polymer composition is fixed with the cumulative structure by the self-organization being maintained, and thus, it is also a preferred embodiment to include a molecule in which a plurality of side chains including the polymerizable group is included in one molecule, or at the time of polymerization, a plurality of the above-described polymerizable groups is included in one molecule, that is, a crosslinkable molecule.

Another embodiment of the present invention is a process for preparing a polymer composition, comprising polymerizing a composition comprising a compound represented by General Formula (1) wherein M is a monovalent or higher valent metal ion which may have a ligand, and at least one of $R_1$ to $R_5$ includes a polymerizable group; eluting a metal salt thereof; and substituting M with a hydrogen atom.

In addition, another embodiment of the present invention is a process for preparing a polymer composition comprising: polymerizing a composition comprising a compound represented by General Formula (1) in which M is a monovalent or higher valent metal ion which may have a ligand, and a compound represented by General Formula (3) in which at least one of both compounds has a polymerizable group; eluting a metal salt thereof; and substituting M with a hydrogen atom.

In addition, another embodiment of the present invention is a method of selectively capturing a metal ion using the polymer composition obtained by the above process for preparing a polymer composition.

Although it is not intended to be bound to a theory, the compound represented by General Formula (1) in which M is a monovalent or higher valent metal ion which may have a ligand forms a composition including a functional substituent introduced at 3-position of the acetylacetone group, or coordination to M by a coexistent compound such as the compound represented by General Formula (3), and the like, also the composition is phase-separated by the functional substituent, thereby preferably having a cumulative structure in the composition. Incidentally, when the compound has the polymerizable group, or the coexistent compound has the polymerizable group, it is possible to fix the anisotropic orientation state of the phase separation structure and the cumulative structure, whereby it is possible to form a stable mold structure of the metal ion M, which is thus preferred.

The polymerizable group may include an ethynyl group, a propargyl group, a vinyl group, an allyl group, a vinylphenyl group, an acryloyl group, a methacryloyl group, an epoxy group, a glycidyl group, a butanedienyl group, a sorbyl group, and the like, and since the nonpolar butanedienyl group does not cause a big change in the hydrophobicity or three-dimensional structure, even in the case of being included at the end of the long chain alkyl group, it is expected that an unstable liquid crystal phase structure is easily reproduced, and polymerization is performed while the anisotropic structure is maintained. In addition, though the acryloyl group and the like are polar groups, a crosslinkable compound including other functional acryloyl group coexists to proceed with a crosslinking reaction at high speed, thereby obtaining a high molecular weight crosslinked polymerized product while maintaining the anisotropic structure. Therefore, the polymerizable group is appropriately selected, depending on what polymerized product is needed.

In addition, the anisotropic orientation state is formed by fixing in the course of polymerization of the composition, and as a result, a mold structure function to allow the compound to selectively capture the metal ion M when eluting the metal ion M can be expressed. The process for preparing a polymer composition of the present invention includes a series of preparing processes.

One embodiment of the present invention is a process for preparing a polymer composition comprising: polymerizing a composition comprising an organic metal compound in which M represented by General Formula (1) is a lithium ion, and at least one of $R_1$ to $R_5$ includes a polymerizable group; then eluting the lithium ion with hydrochloric acid; and substituting M with a hydrogen atom. The thus-obtained polymer composition has a function of recovering only the lithium salt with high selectivity from seawater including a sodium salt dissolved in a large amount and the lithium salt thinly dissolved therein. Therefore, when a similar operation is performed depending on other metals, a polymer composition capable of recovering the metal with high selectivity is obtained.

As the specific operation, it is preferred to completely dissolve the compound represented by General Formula (1), and a base (e.g., sodium hydroxide, potassium hydroxide, potassium carbonate, pyridine, triethylamine, diazabicycloundecanone, and the like) having the same equivalent or more which can sufficiently dissociate the salt of metal ion M (e.g., hydrochloride, hydrobromide, phosphate, nitrate, carbonate, sulfate, and the like) having the same equivalent or more to be captured and the compound represented by General Formula (1) in an appropriate solvent (e.g., water, methanol, ethanol, dimethylformamide, dimethylsulfoxide, and the like, and a mixture thereof).

Then, generally, the produced organic metal salt is separated by distillation removal of a solvent or addition of a poor solvent and/or cooling operation; polymerization is performed in a solution state by heat, ultraviolet rays, and the like, and then thinning is performed by a coating method or fine particles are formed in the course of polymerization, thereby capable of obtaining a polymer composition having a desired form.

The preferred polymer composition is obtained by forming a liquid crystal phase structure, and fixing the phase separation structure and cumulative structure by polymerization. Here, an orientation order degree of the liquid crystal phase structure depends on temperature, and the lower the temperature, the higher the order degree, and thus, it is preferred to perform polymerization at a low temperature.

Hereinafter, the process for preparing the compound represented by General Formula (1) of the present invention will be described.

The compound represented by General Formula (1) (wherein M is a hydrogen ion) is synthesized by a condensation reaction of acetylacetone represented by General Formula (4) or a derivative thereof and α-haloacetyl compound or α-halocrotonyl compound represented by General Formula (5). Heating may be performed depending on the reaction rate.

[Chem. 4]

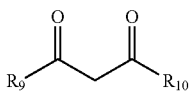

(4)

In Formula (4), $R_9$ and $R_{10}$ are a substituted or unsubstituted alkyl group, aryl group, heterocyclic group, alkenyl group, or alkynyl group, preferably a substituted or unsubstituted alkyl group, aryl group, or heterocyclic group. These groups may include the polymerizable group as described in detail regarding $R_5$.

[Chem. 5]

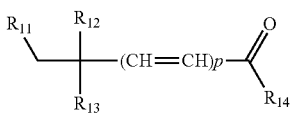

(5)

In Formula (5), $R_{11}$ is a halogen element; $R_{12}$ and $R_{13}$ are a hydrogen atom, or a substituted or unsubstituted alkyl group, aryl group, or heterocyclic group; and $R_{14}$ is a substituted or unsubstituted alkyl group, alkenyl group, alkynyl group, aryl group, heterocyclic group, alkoxy group, aryloxy group, alkylamino group, or arylamino group. These groups may include the polymerizable group described in detail regarding $R_5$. p is 0 or 1.

The halogen element of $R_{11}$ may include chlorine, bromine, and iodine, and chlorine and bromine are preferred.

$R_9$ and $R_{10}$ of Formula (4) correspond to $R_1$ and $R_2$ of Formula (1), respectively. In addition, $R_{12}$, $R_{13}$, and $R_{14}$ of Formula (5) correspond to $R_3$, $R_4$, and $R_5$ of Formula (1), respectively. Therefore, the substituted or unsubstituted alkyl group, aryl group, heterocyclic group, alkenyl group, or alkynyl group in $R_9$ and $R_{10}$, the substituted or unsubstituted alkyl group, aryl group, or heterocyclic group in $R_{12}$ and $R_{13}$, and the substituted or unsubstituted alkyl group, alkenyl group, alkynyl group, aryl group, heterocyclic group, alkoxy group, aryloxy group, alkylamino group, arylamino group in $R_1$ are as similarly described regarding $R_1$ to $R_5$ of Formula (1).

Each of $R_9$ and $R_{10}$ of General Formula (4), and $R_{12}$, $R_{13}$, and $R_{14}$ of General Formula (5) does not include the polymerizable group, or at least one of them includes the polymerizable group.

The polymerizable group may include an ethynyl group, a propargyl group, a vinyl group, an allyl group, a vinylphenyl group, an acryloyl group, a methacryloyl group, an epoxy group, a glycidyl group, a butanedienyl group, a sorbyl group, and the like. These polymerizable groups may not be included, however, are included preferably in at least one of $R_9$, $R_{10}$, and $R_{12}$ to $R_{14}$, more preferably included in $R_{14}$, and still more preferably at the end of $R_{14}$.

In General Formula (5), p is 1 or 0. However, when p=0, $R_{14}$ is not an alkoxy group having 4 or less carbon atoms.

It is preferred that the solvent used in the reaction is an aprotic solvent having no nucleophilicity. For example, chloroform, dichloromethane, 1,2-dichloroethane, toluene, acetonitrile, tetrahydrofuran, acetone, methylethylketone, cyclohexanone, hexamethyl phosphoric triamide, N,N-dimethyl formamide, N,N-dimethyl acetamide, N,N-dimethyl imidazolidinone, N-methyl pyrrolidone, N,N'-dimethylpropylene urea, or dimethyl sulfoxide is preferably used.

As a preparation condition of the compound, particularly when a functional group having a functionality, for example, a polymerizable group is present in the molecule, it is preferred in the preparation method of the present invention to react a reactive acetylacetone derivative having low pKa in the final step, and thus, a reaction condition in which the reaction rapidly proceeds at a mild and low temperature is preferred. The present inventors reviewed the reaction condition in detail from this point of view, and found that the reaction condition is greatly influenced by the type of base to be used, and the presence or absence of an iodine salt.

As the base, an inorganic base or organic base can be used, and the inorganic base may include sodium hydroxide, lithium hydroxide, and potassium hydroxide. In the preparation method b of the present invention, it is more preferred to use an organic base. As the organic base, for example, triethylamine, diazabicyclononene (1,5-diazabicyclo[4.3.0] non-5-ene), or diazabicycloundecene (1,8-diazabicyclo [5.4.0]undeca-7-ene) is preferably used, and in particular dimethylaminopyridine is preferred.

In addition, when the iodine salt coexists in a reaction system, the reaction is promoted, which is thus, preferred. As the iodine salt, potassium iodide or tetrahexylammonium iodide, and tetraethylammonium iodide are preferably used. Here, the iodine salt often has a low solubility in the solvent to be used in the reaction, and in this case, it is preferred that a small amount of water coexist to dissolve the iodine salt.

Since water is a protic solvent, hydrolysis concurrently occurs as a side reaction in a basic system, and thus, it is preferred to maintain the reaction system as neutral as possible. Actually when the acetylacetone derivative having low pKa is used for the reaction raw material, salt formation with the base to be used is predicted in advance to adjust an equivalent property.

In a preferred aspect of the present invention, $R_{14}$ includes a divalent residue represented by the following General Formula (2):

[Chem. 6]

(2)

In Formula (2), k is 2 or 3, and preferably 2. m is an integer of 1 to 20, preferably 2 to 10, and more preferably 3 to 6.

As the appropriate base, when the compound represented by General Formula (4) or General Formula (5) is a material suspicious of basic hydrolysis, such as an ester group, a protic solvent and a hydroxide or carbonate of alkali metals which produce water by condensation are avoided, and an aprotic solvent such as acetone and an organic base (e.g., triethylamine, diazabicyclononane, and the like) or an alkali metal hydride (e.g., sodium hydride and the like) are preferably used.

The compound represented by General Formula (1) (wherein M is a hydrogen ion) obtained as described above is dissolved in water or an organic solvent (methanol, ethanol, isopropanol, and the like), almost the same equivalent of base (lithium hydroxide, lithium carbonate, sodium hydroxide, or sodium hydride) is added to the obtained solution, and after stirring for a predetermined time, the solvent is removed by distillation, and dried in vacuo, thereby capable of obtaining a lithium salt of sodium salt of the compound represented by General Formula (1). As a general method other than this, the compound represented by General Formula (1) or the polymer composition is dissolved and dispersed in an aqueous solution in which the metal salt to be captured is dissolved in a buffer solution capable of completely dissociating the compound, or a mixed solution with an organic solvent, thereby forming the desired metal salt, and separating the metal salt by an appropriate method.

Otherwise, the aqueous solution in which the metal salt to be captured is dissolved or the mixed solution with the organic solvent is brought into contact with the compound represented by General Formula (1) or the solid (fine particles or thin film) of the polymer composition having pKa to be completely dissociated at the pH of the solution, and an appropriate condition such as the condition of substitution of metal with hydrogen in the mixed solution is set, thereby capable of obtaining the desired metal salt.

Hereinafter, specific examples of the compounds represented by General Formula (1) to General Formula (5) will be given, however, the present invention is not limited thereto.

[Chem. 7]

(1)-1

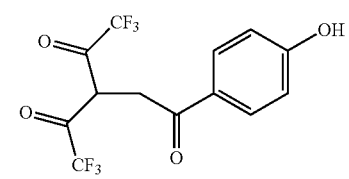

(1)-2

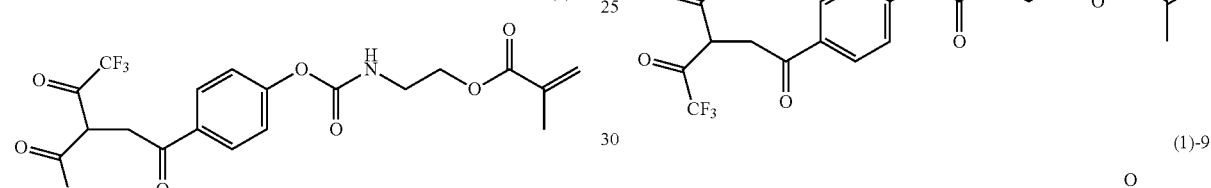

(1)-3

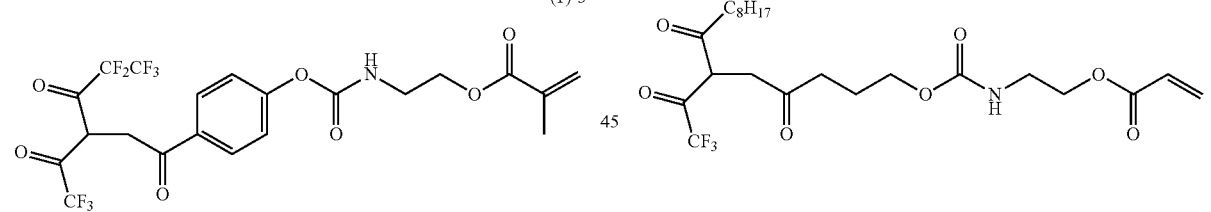

(1)-4

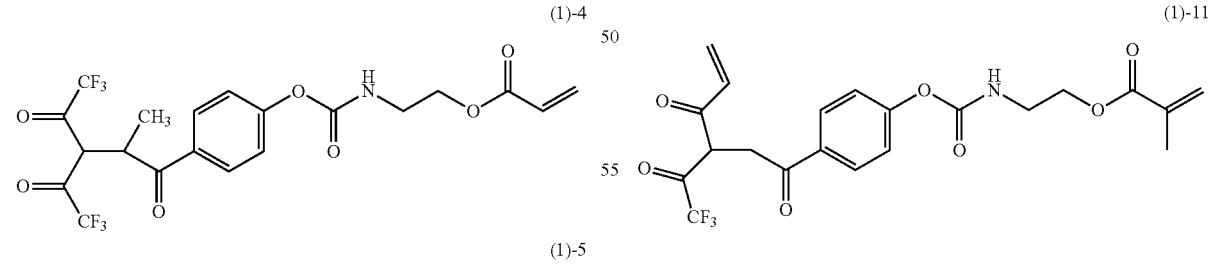

(1)-5

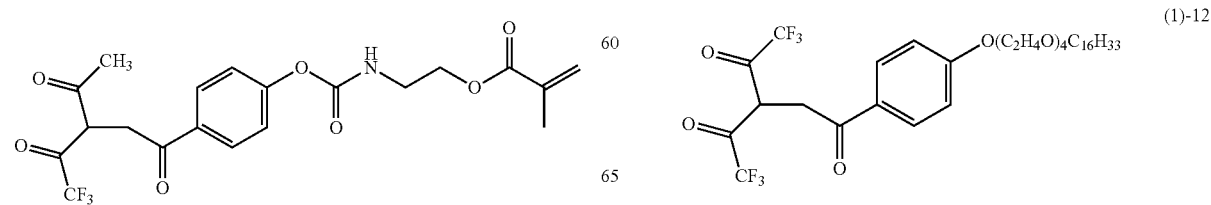

(1)-6

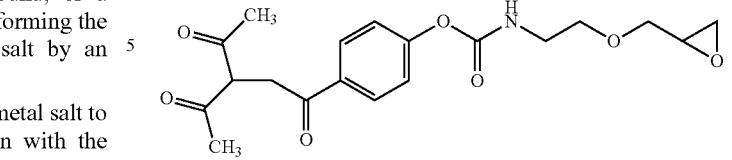

(1)-7

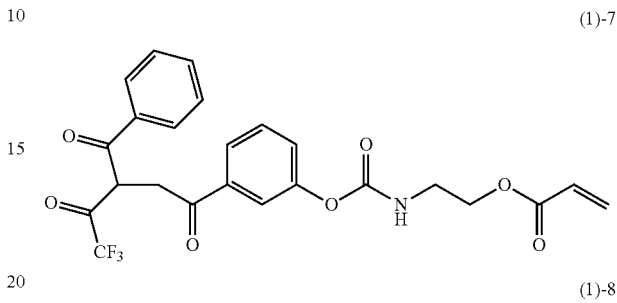

(1)-8

(1)-9

(1)-10

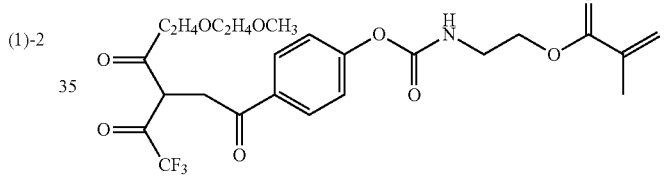

(1)-11

(1)-12

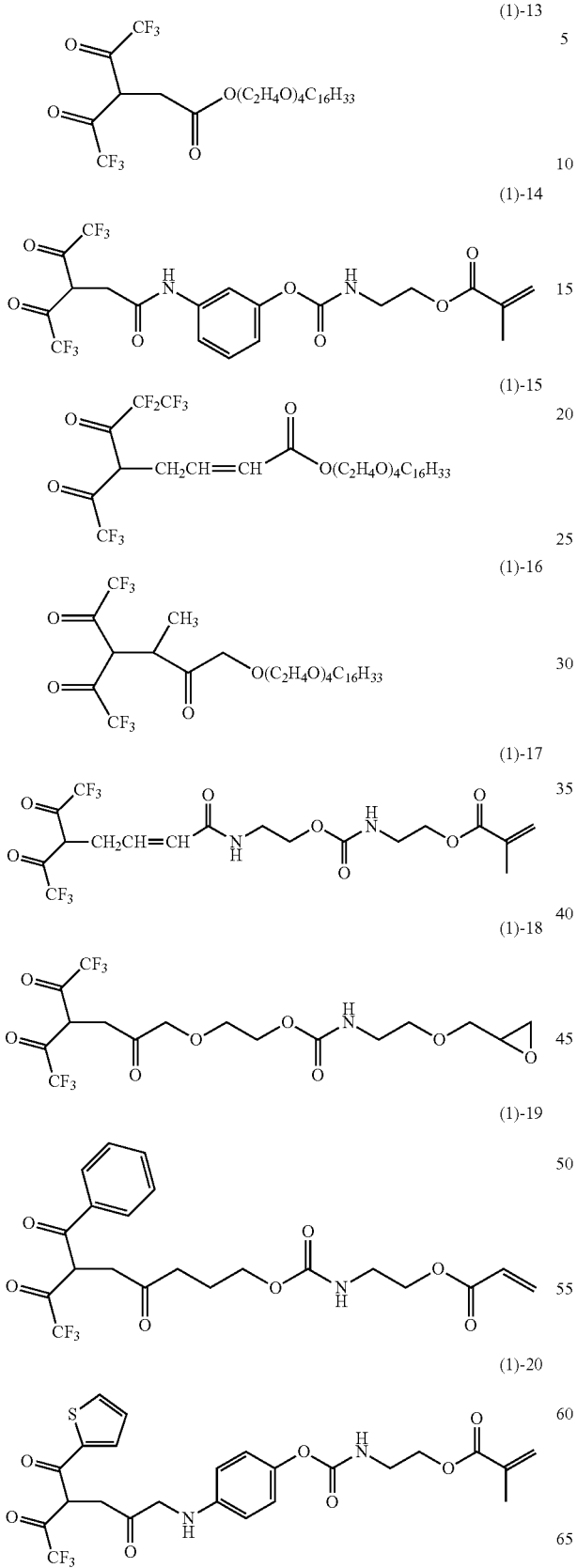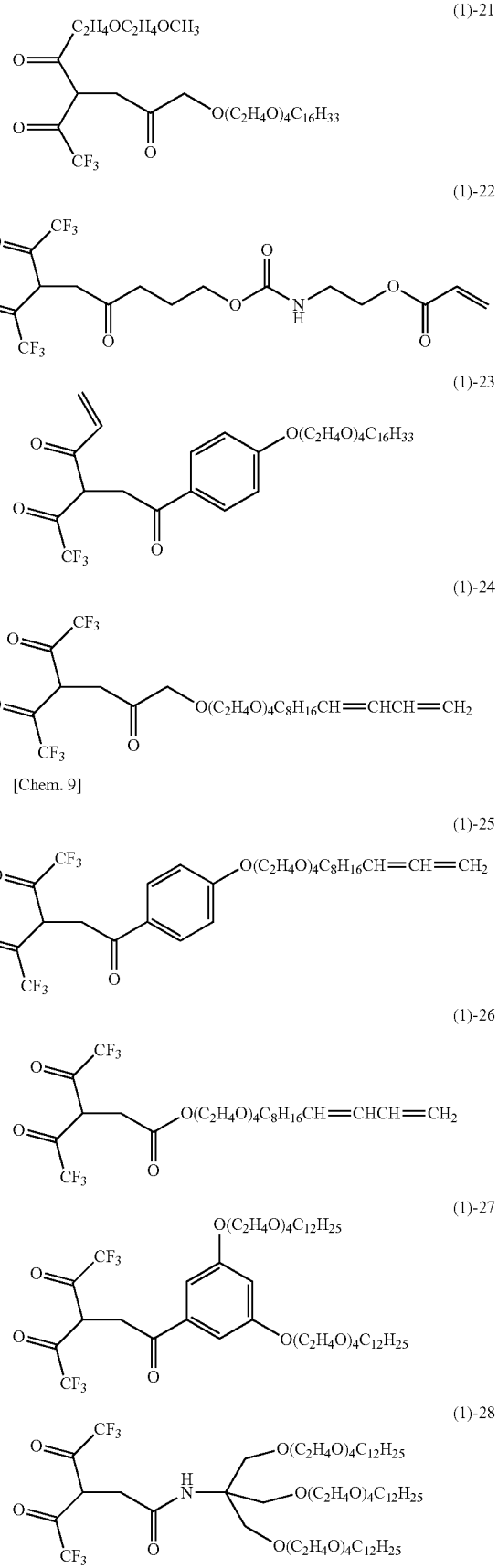

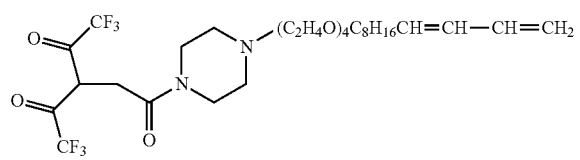
(1)-29

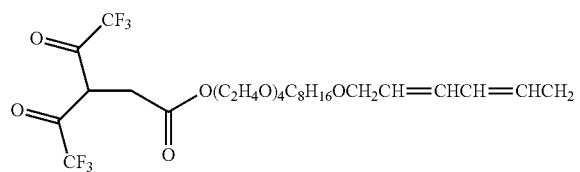
(1)-30

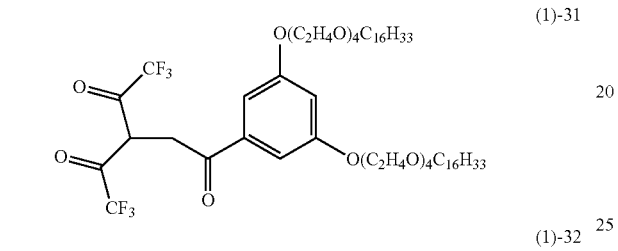
(1)-31

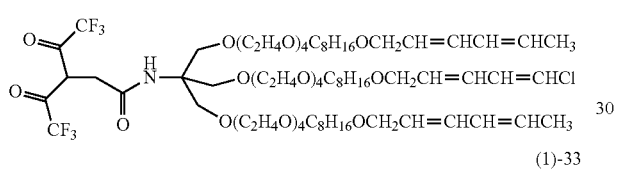
(1)-32

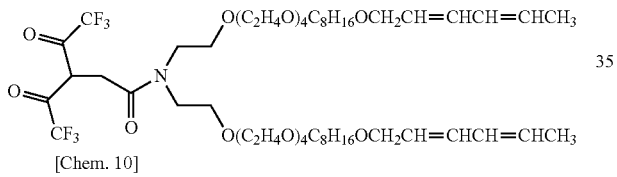
(1)-33

[Chem. 10]

—(CH₂CH₂O)₄— (2)-1

—(CH₂CH₂O)₃— (2)-2

—(CH₂CH₂O)₁₀— (2)-3

—(CH₂CH₂CH₂O)₃— (2)-4

[Chem. 11]

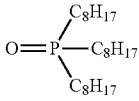
(3)-1

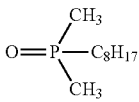
(3)-2

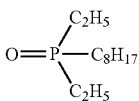
(3)-3

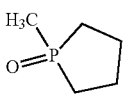
(3)-4

(3)-5

$$O=P\begin{array}{l}C_3H_6OCH_2CH=CH_2\\C_3H_6OCH_2CH=CH_2\\C_3H_6OCH_2CH=CH_2\end{array}$$

(3)-6

[diphenyl(methyl)phosphine oxide structure]

(3)-7

[1,2-bis(methyl(allyl)phosphinyl)ethane structure]

(3)-8

[1,2-bis(dipentylphosphinyl)ethane structure]

(3)-9

[1,2-bis(diisopropylphosphinyl)benzene structure]

(3)-10

[1,2-bis(dibutylphosphinyl)benzene structure]

[Chem. 12]

(4)-1

$$F_3C\underset{O}{\overset{O}{\|}}\hspace{-2pt}\overset{\phantom{O}}{\phantom{|}}\hspace{-4pt}\underset{\phantom{O}}{\overset{O}{\|}}CF_3$$

(4)-2

$$F_3C\underset{O}{\overset{O}{\|}}\hspace{-2pt}\overset{\phantom{O}}{\phantom{|}}\hspace{-4pt}\underset{\phantom{O}}{\overset{O}{\|}}CF_2CF_3$$

(4)-3

$$F_3C\underset{O}{\overset{O}{\|}}\hspace{-2pt}\overset{\phantom{O}}{\phantom{|}}\hspace{-4pt}\underset{\phantom{O}}{\overset{O}{\|}}CH_3$$

(4)-4

$$H_3C\underset{O}{\overset{O}{\|}}\hspace{-2pt}\overset{\phantom{O}}{\phantom{|}}\hspace{-4pt}\underset{\phantom{O}}{\overset{O}{\|}}CH_3$$

(4)-5

[1-(1,3,4-thiadiazol-2-yl)-4,4,4-trifluorobutane-1,3-dione structure]

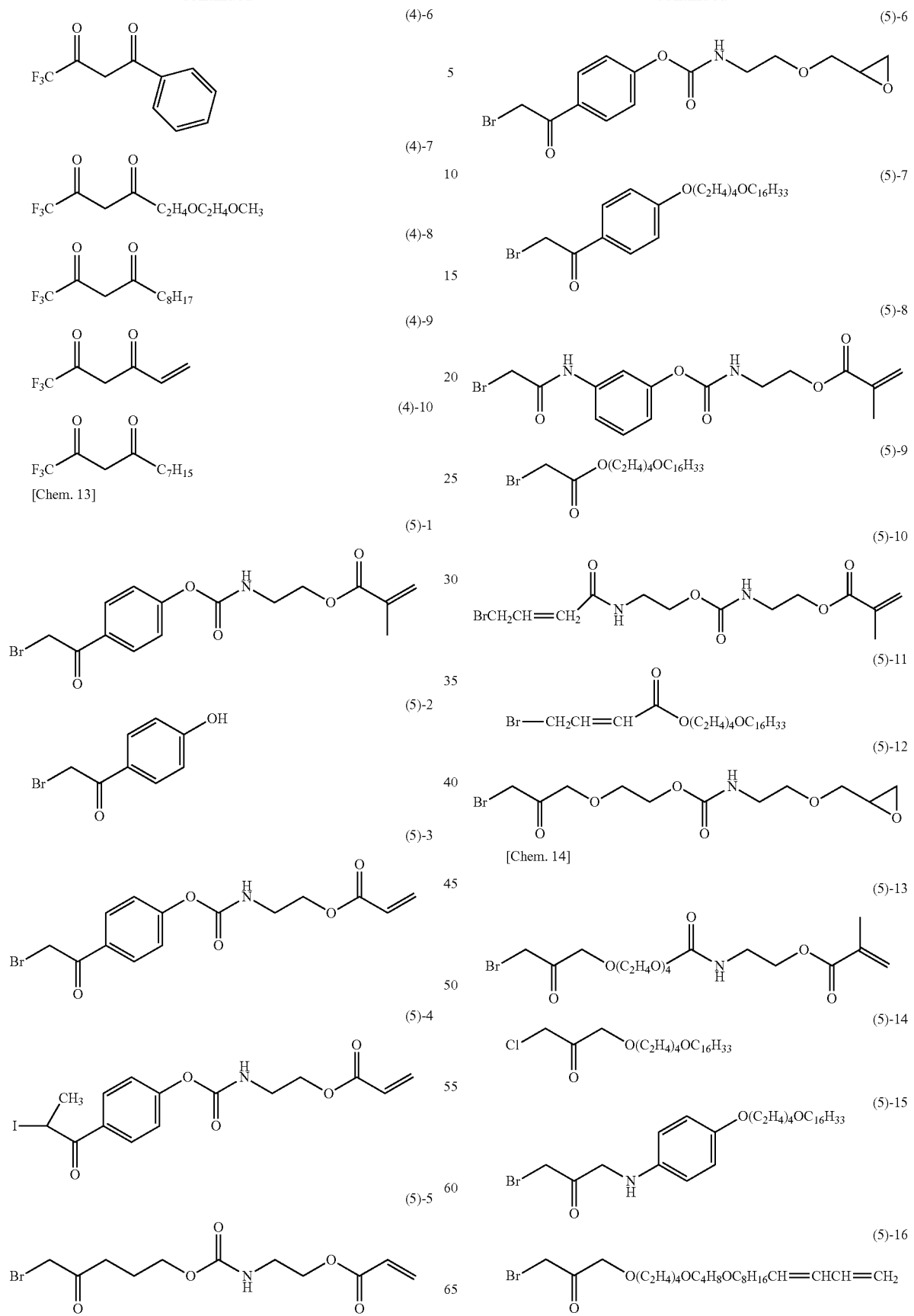

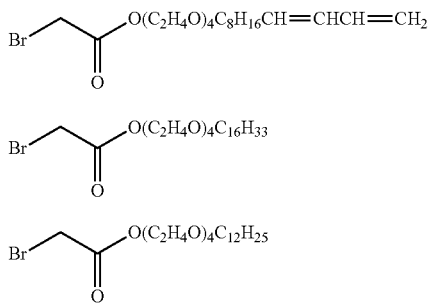

(5)-17

(5)-18

(5)-19

EXAMPLES

Hereinafter, the present invention will be described in detail, by the Examples, however, the present invention is not limited to these Examples.

<Material and Synthesis>

In the following Examples, the reagent and the solvent were all obtained from Aldrich Chemical Company, Inc., Tokyo Chemical Industry Co., Ltd., or Wako Pure Chemical Industries, Ltd.

<Instrumental Analysis>

1H- and 13C{1H}-NMR spectra were measured using a JNM-ECX400Delta V5 spectrometer manufactured by JEOL Ltd.

FT-IR spectrum was measured using an IRT-5000 microscope manufactured by JASCO Corporation equipped with a FP82HT hot stage controlled by a FP-90 Central Processor manufactured by METTLER TOLEDO, and a FT-IR6100 spectrometer manufactured by JASCO Corporation.

An X-ray diffraction (XRD) pattern was measured by a RINT-2500 diffraction device manufactured by Rigaku Corporation equipped with a heating device, using a ray source: CuKα ray.

Compounds (1)-1, (1)-2, and (1)-13 were obtained using a synthesis route represented by the following Scheme 1:

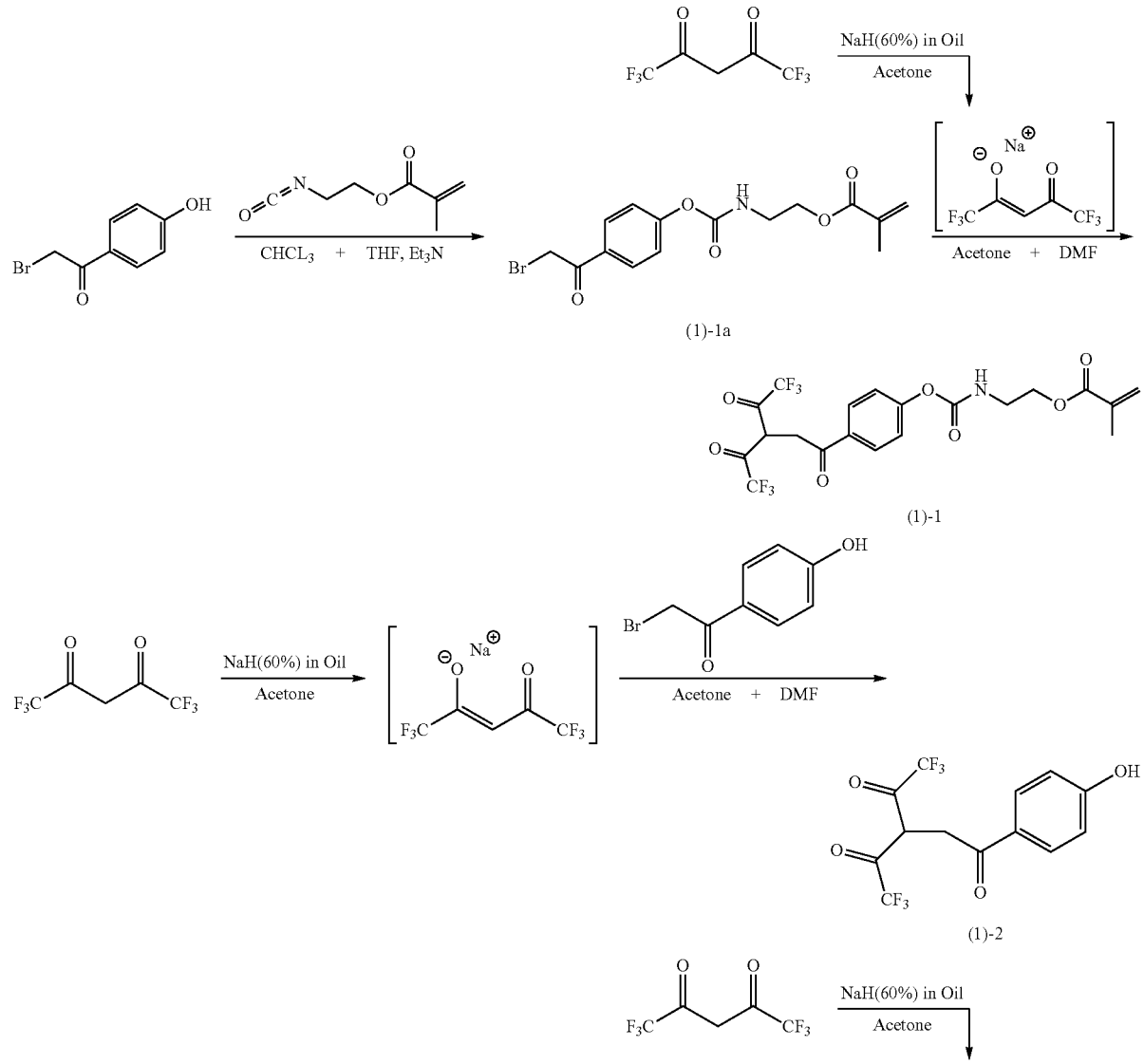

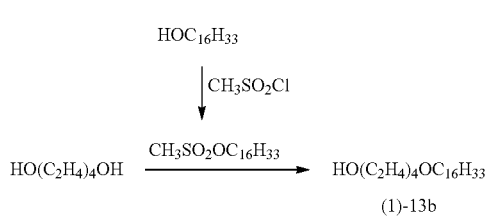

-continued

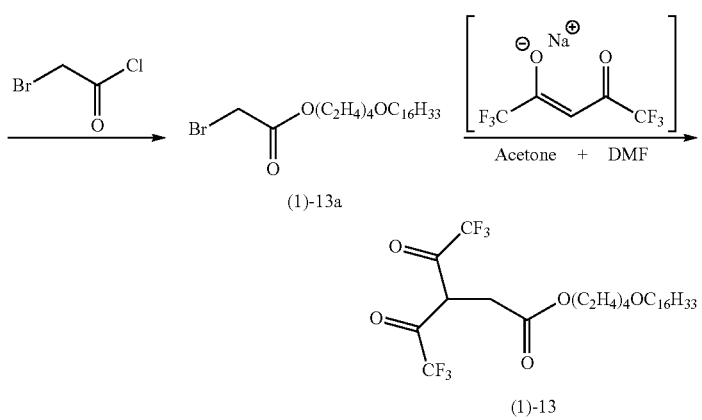

Synthesis Example 1

Synthesis of compound (1)-1

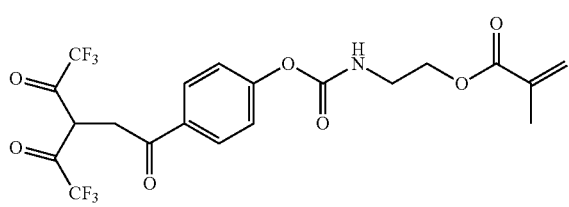

Step 1: Synthesis of 2-(((4-(2-bromoacetyl)phenoxy)carbonyl)amino)ethyl methacrylate (1)-1a To a dried tetrahydrofuran (4.0 mL) solution of 2-bromo-1-(4-hydroxyphenyl)ethane-1-one (2.23 g, 10.4 mmol) and 2-isocyanoethyl methacrylate (1.60 mL, 11.3 mmol), triethylamine (0.35 mL, 2.5 mmol) was slowly added at 0° C. Thereafter, the mixture was stirred at room temperature for 3 hours. The reaction mixture was added to dilute hydrochloric acid (ca. 5%), and the product was extracted with ethyl acetate. An organic phase was washed with water, and then dried with anhydrous sodium sulfate. The solvent was removed by distillation after filtration, and then a crude produce was purified with column chromatography (silica, n-hexane:ethyl acetate (2:1)), and dried in vacuo, thereby obtaining the title compound as a white solid (yield amount of 3.01 g, yield rate of 81%).

$^1$H NMR (400 MHz, DMSO, δ): 8.10 (t, 1H), 7.95 (d, 2H), 7.25 (d, 2H), 6.06 (d, 1H), 5.65 (d, 1H), 4.88 (s, 2H), 4.15 (t, 2H), 3.35 (t, 2H), 1.84 (s, 3H) $^{13}$C NMR (100 MHz, CDCl$_3$, δ): 191.16, 167.07, 155.79, 154.30, 136.31, 131.25, 130.98, 130.31, 126.58, 122.66, 122.34, 63.60, 34.56, 18.53 IR (neat) cm$^{-1}$: 3355.5, 2955.4, 1741.4, 1716.3, 1682.6, 1636.3, 1601.6, 1638.0, 1500.4, 1455.0, 1434.8, 1413.6, 1320.0, 1298.8, 1281.5, 1215.9, 1197.6, 1167.7, 1110.8, 1040.4, 1011.5, 993.2, 951.7, 852.4, 815.7, 761.7, 701.0

Step 2: Synthesis of 2-(((4-(5,5,5-trifluoro-4-oxo-3-(2,2,2-trifluoroacetyl)pentanoyl)phenoxy)carbonyl)amino)ethyl methacrylate (1)-1

To an acetone (5.0 mL) solution of 1,1,1,5,5,5-hexafluoropentane-2,4-dione (1.15 mL, 8.13 mmol), sodium hydride in oil (60%) (0.324 g, 8.1 mmol) was slowly added at 0° C. After stirring for 30 minutes, 2-(((4-(2-bromoacetyl)phenoxy)carbonyl)amino)ethyl methacrylate (1.5 g, 4.05 mmol) was added thereto. Thereafter, to this mixture, dimethyl formamide (15 mL) was added, and stirred at 100° C. for 10 hours. To the reaction mixture, 50 mL of n-hexane:ethyl acetate (2:1) was added, stirred at 0° C. for 2 hours, and then a produced white precipitate was filtered. This was dissolved in ethyl acetate (10 mL) by heating, stirred in methanol/ice bath for 2 hours, allowed to stand for 30 minutes, and a supernatant was decanted. This operation was repeated 6 times, thereby obtaining the title compound as a white solid (yield amount of 0.30 g, yield rate of 15%)

$^1$H NMR (400 MHz, DMSO, δ): 8.05 (t, 1H), 7.95 (d, 2H), 7.20 (d, 2H), 6.06 (d, 1H), 5.65 (d, 1H), 5.04 (t, 1H), 4.75 (d, 2H), 4.15 (t, 2H), 3.35 (t, 2H), 1.84 (s, 3H) $^{13}$C NMR (100 MHz, CDCl$_3$, δ): 198.60, 167.08, 155.40, 154.40, 154.26, 136.31, 131.90, 129.74, 126.57, 122.59, 122.27, 122.12, 70.31, 65.81, 63.61, 18.51 IR (neat) cm$^{-1}$: 3428.8, 3377.7, 3323.7, 3071.1, 2959.2, 2935.1, 2899.5, 2791.5, 1713.4, 1681.6, 1638.2, 1602.6, 1545.7, 1501.6, 1451.2, 1420.3, 1338.4, 1296.9, 1271.8, 1226.5, 1171.5, 1110.8, 978.7, 860.1, 814.8

Synthesis Example 2

Synthesis of Compound (1)-2

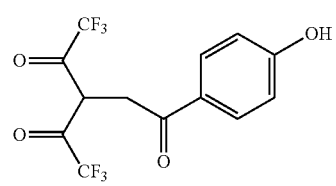

Step 1: Synthesis of 5,5,5-trifluoro-1-(4-hydroxyphenyl)-3-(2,2,2-trifluoroacetyl)pentane-1,4-dione (1)-2

To an acetone (10.0 mL) solution of 1,1,1,5,5,5-hexafluoropentane-2,4-dione (5.31 mL, 37.5 mmol), potassium hydroxide (2.18 g, 38.9 mmol) and polyethylene glycol 400 (0.75 mL) were added at room temperature. After stirring for 2 hours, 2-bromo-1-(4-hydroxyphenyl)ethane-1-one (8.065 g, 37.5 mmol) was added thereto. Thereafter, the mixture was heated to reflux for 10 hours. After concentrating the reaction mixture, dilute hydrochloric acid (ca. 5%) was added, and the product was extracted with ethyl acetate. An organic phase was washed with water, and then dried with anhydrous sodium sulfate. The solvent was removed by distillation subsequent to filtration, and then a crude product was purified with column chromatography (silica, chloroform:ethyl acetate (2:1)), and dried in vacuo, thereby obtaining the title compound as a white solid (yield amount 13.1 g, yield rate 70%).

$^1$H NMR (400 MHz, DMSO, δ): 10.35 (s, 1H), 7.80 (d, 2H), 6.86 (d, 2H), 4.90 (t, 1H), 4.70 (d, 2H), $^{13}$C NMR (100 MHz, CDCl$_3$, δ): 197.64, 162.74, 130.61, 126.54, 115.84, 65.32

IR (neat) cm$^{-1}$: 3417.2, 3250.4, 1676.8, 1606.4, 1592.9, 1518.7, 1456.0, 1413.6, 1312.3, 1279.5, 1227.5, 1171.5, 1115.6, 1088.6, 978.7, 833.1, 700.0

Synthesis Example 3

Synthesis of Compound (1)-13 anhydrous sodium sulfate. After the solvent was removed by distillation subsequent to filtration, a crude product was purified with column chromatography (silica, ethyl acetate), and dried in vacuo, thereby obtaining (1)-13b as a white solid (yield amount of 13.6 g, yield rate of 60%).

$^1$H NMR (400 MHz, CDCl$_3$, δ): 3.71 (t, 2H), 3.55-3.68 (m, 14H), 3.43 (t, 2H), 1.55 (t, 2H), 1.25 (s, 26H), 0.86 (t, 3H)

Step 2: Synthesis of 3,6,9,12-tetraoxaoctacosyl 2-bromoacetate (1)-1a

To a dichloromethane (9.0 mL) solution of 3,6,9,12-tetraoxaoctacosane-1-ol (5.0 g, 11.9 mmol), triethylamine (2.8 mL, 20.2 mmol) was added. Bromoacetyl chloride (1.5 mL, 17.9 mmol) was slowly added thereto at −78° C. After stirring for 3 hours, the temperature was returned to room temperature overnight. Dilute hydrochloric acid (ca. 5%) was added, and the product was extracted with dichloromethane. An organic phase was washed with water, and then dried with anhydrous sodium sulfate. After the solvent was removed by distillation subsequent to filtration, a crude

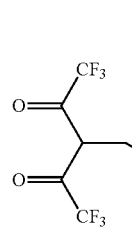

(1)-13

Step 1: Synthesis of 3,6,9,12-tetraoxyoctacosane-1-ol (1)-13b

To a tetrahydrofuran (250 mL) solution of hexadecanol (84.3 g, 348 mmol), methanesulfonyl chloride (41.84 g, 365 mmol) was slowly added under ice cooling, and then pyridine (30.0 mL, 365 mmol) was added thereto. Thereafter, the mixture was stirred at room temperature for 10 hours. The reaction mixture was concentrated, and added to dilute hydrochloric acid (ca. 5%), and the product was extracted with ethyl acetate. An organic phase was washed with water, and then dried with anhydrous sodium sulfate. The solvent was removed by distillation subsequent to filtration, and the product was dried in vacuo, thereby obtaining hexadecylmethane sulfonate as a colorless solid.

To tetraethylene glycol (35.6 g, 183 mmol), t-butoxy potassium (6.06 g, 54.0 mmol) was added at room temperature, stirred for 30 minutes, and then heated at 140° C. 2-bromo-1-(4-hydroxyphenyl)ethane-1-one (8.065 g, 37.5 mmol) was added thereto. To the mixture, hexadecylmethane sulfonate (17.3 g, 54.0 mmol) was added in four portions, and then heated again for 5 hours. After cooling the reaction mixture, dilute hydrochloric acid (ca. 5%) was added, and the product was extracted with ethyl acetate. An organic phase was washed with water, and then dried with product was purified with column chromatography (silica, ethyl acetate:chloroform (1:9)), and dried in vacuo, thereby obtaining (1)-13a as a light yellow waxy solid (yield amount of 4.7 g, yield rate of 73%).

$^1$H NMR (400 MHz, CDCl$_3$, δ): 4.32 (t, 2H), 4.10 (s, 2H), 3.72 (t, 2H), 3.63-3.65 (m, 10H), 3.57 (t, 2H), 3.43 (t, 2H), 1.57 (m, 2H), 1.15-1.30 (m, 26H), 0.85 (t, 3H)

IR (neat) cm$^{-1}$: 2952.5, 2917.8, 2850.3, 1756.8, 1467.6, 1415.5, 1376.9, 1351.9, 1293.0, 1251.6, 1184.1, 1133.0, 1036.6, 963.3, 870.7, 780.1, 721.2

Step 3: Synthesis of 3,6,9,12-tetraoxaoctacosyl 5,5,5-trifluoro-4-oxo-3-(2,2,2-trifluoroacetyl)pentanoate (1)-13

To a tetrahydrofuran (5.0 mL) solution of 1,1,1,5,5,5-hexafluoropentane-2,4-dione (0.539 mL, 3.81 mmol), sodium hydride in oil (60%) (0.148 g, 3.7 mmol) was slowly added at 0° C. After stirring for 30 minutes, 2-(((4-(2-bromoacetyl)phenoxy)carbonyl)amino)ethyl methacrylate (1.0 g, 1.85 mmol) was added thereto. Thereafter, the mixture was stirred at 120° C. for 24 hours. The reaction mixture was added to dilute hydrochloric acid (ca. 5%), and the product was extracted with ethyl acetate. An organic phase was washed with water, and then dried with anhydrous sodium sulfate. After the solvent was removed by distillation subsequent to filtration, a crude product was purified with column chromatography (silica, chloroform:ethyl acetate (3:1)), and dried in vacuo, thereby obtaining (1)-13 as a light brown solid (yield amount of 0.60 g, yield rate of 24%).

$^1$H NMR (400 MHz, CDCl$_3$, δ): 4.40 (t, 1H), 4.30-4.36 (m, 2H), 3.77 (t, 1H), 3.71 (t, 1H), 3.60-3.66 (m, 8H), 3.56 (m, 2H), 3.43 (t, 2H), 1.5-1.58 (m, 2H), 1.20-1.32 (m, 14H), 0.85 (t, 3H) $^{13}$C NMR (100 MHz, CDCl$_3$, δ): 198.71, 168.92, 167.46, 162.59, 158.61, 158.34, 157.92, 157.66, 101.38, 71.64, 70.71, 70.66, 70.60, 70.04, 69.17, 68.82, 68.46, 65.91, 65.24, 63.68, 63.23, 63.17, 40.90, 31.98, 29.75, 29.67, 29.60, 29.54, 29.41, 27.00, 26.11, 22.74, 14.17, 13.97 IR (neat) cm$^{-1}$: 3448.1, 2951.5, 2917.8, 2850.3, 1750.1, 1637.3, 1467.6, 1377.9, 1350.9, 1323.9, 1278.6, 1223.9, 1101.6, 1039.4, 991.2, 951.7, 871.7, 721.2

Synthesis Example 4

Synthesis of Compound (1)-26

Step 1: Synthesis of 3,6,9,12-tetraoxatetracosyl-21,23-dienyl-1-ol (1)-26b

To a tetrahydrofuran (250 mL) solution of 1,3-dienyl-12-iodiundecane (4.0 g, 13.7 mmol) and tetraethylene glycol (8.0 g, 41.6 mmol), sodium hydride (0.56 g, 14.0 mmol) was added under ice cooling, stirred for 3 hours, and heated at 40° C. for 24 hours. After cooling the reaction mixture, dilute hydrochloric acid (ca. 5%) was added thereto, and the product was extracted with ethyl acetate. An organic phase was washed with water, and then dried with anhydrous sodium sulfate. After the solvent was removed by distillation subsequent to filtration, a crude product was purified with column chromatography (silica, ethyl acetate), and dried in vacuo, thereby obtaining (1)-26b as a colorless liquid (yield amount of 3.49 g, yield rate of 71%).

$^1$H NMR (400 MHz, CDCl$_3$, δ): 6.30 (m, 1H), 6.05 (m, 1H), 5.70 (m, 1H), 5.10 (d, 1H), 4.95 (d, 1H), 3.73 (t, 2H), 3.65 (m, 8H), 3.60 (t, 2H), 3.45 (t, 2H), 3.20 (br, 1H) 2.06 (t, 2H), 1.5-1.58 (m, 2H), 1.20-1.32 (m, 10H), 13C NMR (400 MHz, CDCl$_3$, δ): 137.5, 136.0, 131.0, 115.0, 73.0, 71.8, 71.0, 70.8, 70.0, 62.0, 61.0, 55.0, 33.0, 30.5, 30.0, 29.5, 26.5 21.0, 14.5 IR (neat) cm$^{-1}$: 3451.0, 2927.4, 2857.0, 1694.2, 1650.8, 1602.6, 1641.8, 1350.9, 1298.8, 1249.7, 1123.3, 1004.7, 950.7, 895.8

Step 2: Synthesis of 3,6,9,12-tetraoxatetracosane-21,23-dienyl 2-bromoacetate (1)-26a (=(5)-17)

3,6,9,12-tetraoxaoctacosyl-21,23-dienyl-1-ol was used to perform synthesis in accordance with the method of (1)-13a, thereby obtaining 3,6,9,12-tetraoxatetracosane-21,23-dienyl 2-bromoacetate (1)-26a (=(5)-17) as a colorless transparent liquid (yield amount of 3.3 g).

$^1$H NMR (400 MHz, CDCl$_3$, δ): 6.30 (m, 1H), 6.05 (m, 1H), 5.70 (m, 1H), 5.10 (d, 1H), 4.95 (d, 1H), 4.33 (m, 2H), 4.10 (s, 1H), 3.88 (s, 1H) 3.73 (t, 2H), 3.65 (m, 8H), 3.60 (t, 2H), 3.43 (t, 2H), 2.06 (t, 2H), 1.5-1.58 (m, 2H), 1.20-1.32 (m, 10H), $^{13}$C NMR (400 MHz, CDCl$_3$, δ): 167.5, 137.5, 136.0, 131.0, 115.0, 71.8, 71.0, 70.8, 69.0, 65.0, 41.0, 33.0, 30.5, 30.0, 29.5, 26.0 IR (neat) cm$^{-1}$: 3084.6, 2927.4, 2856.1, 1756.8, 1741.4, 1650.8, 1602.6, 1454.1, 1350.9, 1285.3, 1121.4, 1037.5, 1004.7, 951.7, 897.7

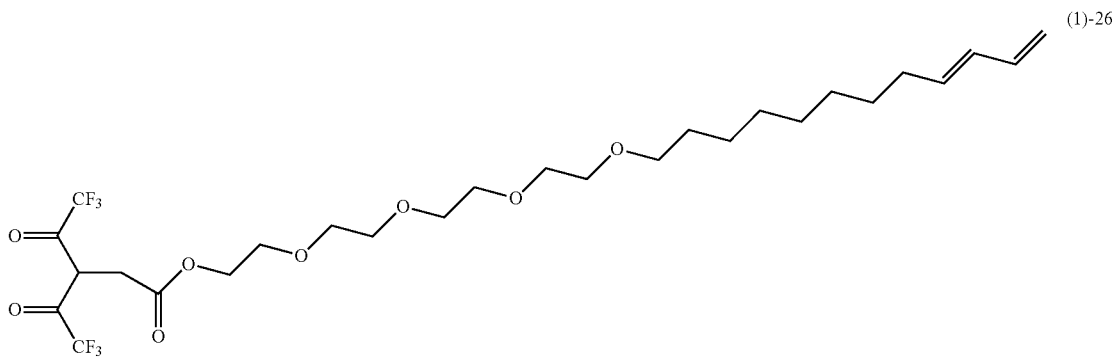 [SMILES: C=C/C=C/CCCCCCCCOCCOCCOCCOCCOC(=O)CC(C(=O)C(F)(F)F)C(=O)C(F)(F)F]

(1)-26

Step 3: Synthesis of 3,6,9,12-tetraoxaoctacosyl-21, 23-dienyl 5,5,5-trifluoro-4-oxo-3-(2, 2, 2-trifluoro-acetyl) pentanoate (1)-26

To an acetone (32.5 mL) solution of 3,6,9,12-tetraoxatetracosane-21,23-dienyl 2-bromoacetate (0.992 mL, 2.07 mmol), 1,1,1,5,5,5-hexafluoropentane-2,4-dione (0.585 mL, 4.06 mmol) was dropped at room temperature, tetraethyl ammonium iodide (0.535 mg, 2.08 mmol) was added again, and then dimethylaminopyridine (0.500 mg, 4.10 mmol) was slowly added. After stirring for 30 minutes, 3.0 mL of water was added. Thereafter, the mixture was stirred for 24 hours. After concentrating the reaction mixture under reduced pressure, a mixture of 3 N hydrochloric acid and ethyl acetate was added, the product was extracted with ethyl acetate, and dried with anhydrous sodium sulfate. After the solvent was removed by distillation subsequent to filtration, a crude product was purified with column chromatography (silica, n-hexane:ethyl acetate (3:2)), dried in vacuo, thereby obtaining (1)-26 as a light yellow viscous liquid (yield amount of 0.77 g, yield rate of 61%).

$^1$H NMR (400 MHz, CDCl$_3$, δ): 6.30 (m, 1H), 6.05 (m, 1H), 5.70 (m, 1H), 5.10 (d, 1H), 4.95 (d, 1H), 4.30-4.36 (m, 2H), 4.10 (s, 1H), 3.73 (t, 2H), 3.65 (m, 8H), 3.60 (t, 2H), 3.43 (t, 2H), 2.06 (t, 2H), 1.5-1.58 (m, 2H), 1.20-1.32 (m, 10H), $^{13}$C NMR (400 MHz, CDCl$_3$, δ): 169.0, 167.5, 137.5, 136.0, 133.0, 132.5, 131.5, 129.5, 116.5, 115.0, 71.8, 70.8, 69.0, 65.0, 41.0, 33.0, 30.5, 30.0, 29.5, 26.5, −5.5 $^{19}$F NMR (400 MHz, CDCl$_3$, δ): −76.0, −87.0 IR (neat) cm$^{-1}$: 3447.1, 3086.3, 2927.4, 2857.0, 1736.6, 1693.2, 1650.8, 1602.6, 1456.0, 1416.5, 1350.9, 1266.0, 1138.8, 1037.5, 1005.7, 962.7, 901.6, 874.6, 783.0, 723.2, 655.7

Example 1

To a methanol solution of the above-synthesized compounds (1)-1, (1)-13, and (1)-26, the same equivalent of lithium hydroxide was added, and stirred for 1 hour, and then the solvent was removed by distillation and dried in vacuo, thereby obtaining the lithium salts of (1)-1, (1)-13, and (1)-26 which are (1)-1L, (1)-13L, and (1)-26L. In addition, for the lithium salt of (1)-1, (1)-1L, a methanol solution to which twice the equivalent of trioctylphosphine oxide (TOPO) was likewise added was stirred for 1 hour, and then the solvent was removed by distillation and dried in vacuo, thereby obtaining a (1)-1L TOPO complex. In addition, the complex was heated at 145° C. for 15 minutes on a silicon substrate, thereby obtaining a heated film of the (1)-1L TOPO complex.

Lithium salt of (1)-1 which is (1)-1L

IR (neat) cm$^{-1}$: 3351.7, 2956.3, 2892.7, 2811.7, 1714.4, 1656.6, 1638.2, 1592.0, 1545.7, 1508.1, 1456.0, 1430.9, 1371.1, 1299.8, 1267.0, 1172.5, 1114.7, 1098.3, 1040.4, 1002.8, 977.7, 946.9, 846.6, 822.5, 781.0, 702.0

Lithium salt of (1)-1 which is (1)-1L TOPO complex

IR (neat) cm$^{-1}$: 3296.7, 2953.5, 2923.6, 2854.1, 1720.2, 1656.6, 1633.4, 1572.7, 1543.7, 1505.2, 1465.6, 1429.0, 1367.3, 1334.5, 1300.8, 1284.4, 1250.6, 1195.7, 1166.7, 1145.5, 1099.2, 999.9, 977.7, 845.6, 823.5, 720.3

Heated film of lithium salt of (1)-1 which is (1)-1L TOPO complex

IR (neat) cm$^{-1}$: 2954.4, 2925.5, 2855.1, 1632.5, 1600.6, 1573.6, 1516.7, 1465.6, 1388.5, 1310.4, 1277.6, 1242.9, 1198.5, 1159.0, 1086.7, 847.6, 794.5, 722.2

Lithium salt of (1)-13 which is (1)-13L

IR (neat) cm$^{-1}$: 3426.9, 2917.8, 2850.3, 1677.8, 1605.5, 1467.6, 1419.4, 1350.9, 1325.8, 1299.8, 1239.0, 1121.4, 945.9, 884.2, 721.2

Lithium salt of (1)-26 which is (1)-26L

IR (neat) cm$^{-1}$: 3447.1, 3084.6, 2927.4, 2857.0, 1649.8, 1602.5, 1457.0, 1435.7, 1350.9, 1297.9, 1259.3, 1180.2, 1122.4, 1003.8, 949.8, 898.7, 789.7, 680.7

In general, β-diketone represents absorption of a conjugated carbonyl group [—CH=CH—C=O](A) at 1660 to 1740 cm$^{-1}$, and it is known that when an equivalent resonance ring structure (B) together with two carbonyl groups is taken by formation of salt with a metal ion such as a lithium ion, broad absorption characteristic at 1550 to 1680 cm$^{-1}$ is given.

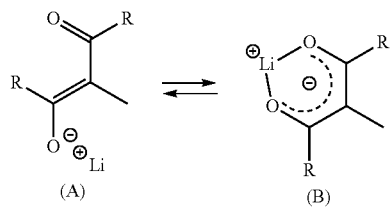

(A)   (B)

The left side of FIG. 1 shows the FT-IR spectra of (1)-1 and the lithium salt thereof, (1)-1L, and also (1)-1L TOPO complex which was formed by adding twice the equivalent of trioctylphosphine oxide (TOPO) to the lithium salt of (1)-1, (1)-1L, and the (1)-1L TOPO complex after heat treatment.

The right side of FIG. 1 shows FT-IR spectra of (1)-13 and the lithium salt thereof which is (1)-13L.

Compound (1)-1 represents absorption of a large conjugated carbonyl group (A) at 1713.4 cm$^{-1}$ and 1681.6 cm$^{-1}$, and the lithium salt also represents absorption of a large conjugated carbonyl group (A) at 1714.4 cm$^{-1}$ and 1656.6 cm$^{-1}$. However, when two equivalents of TOPO are present, the equilibrium is significantly biased to the resonance ring structure (B), and when heating this, it can be seen that the conjugated carbonyl group (A) completely disappears, thereby forming a lithium salt of all stable resonance ring structure (B). That is, it was found that two equivalents of TOPO promote the capture of lithium salt, so that compound (1)-1 has a function of forming a stable lithium salt. Meanwhile, it was found that compound (1)-13 having a tetraethyleneoxy group in the molecule has a function of forming a lithium salt of completely stable resonance ring structure (B) at room temperature alone.

That is, a compound having β-diketone at the end of the molecule can form a thermally stable lithium salt, and maintain lithium alone, or by selecting an appropriate ligand.

Example 2

To a methanol solution of the above-synthesized compounds (1)-1, (1)-13, and (1)-26, the same equivalent of sodium hydride was added, and stirred for 1 hour, and the solvent was removed by distillation, and dried in vacuo, thereby obtaining the sodium salts of (1)-1, (1)-13, and (1)-26 which are (1)-1N, (1)-13N, and (1)-26N.

Sodium salt of (1)-1 which is (1)-1N

IR (neat) cm$^{-1}$: 3539.7, 3346.9, 2956.3, 1719.2, 1656.6, 1640.2, 1592.9, 1565.9, 1510.0, 1453.1, 1429.0, 1320.0, 1300.8, 1261.2, 1214.9, 1169.6, 1110.8, 1087.7, 1039.4, 1000.9, 974.8, 945.0, 842.7, 817.7, 780.1

Heated film of sodium salt of (1)-1 which is (1)-1N TOPO complex

IR (neat) cm$^{-1}$: 3302.5, 2925.5, 1711.5, 1656.6, 1594.8, 1511.0, 1433.8, 1321.0, 1263.2, 1253.5, 1177.3, 1092.5, 999.9, 979.7, 847.6

Sodium salt of (1)-13 which is (1)-13N

IR (neat) cm$^{-1}$: 3290.2, 2952.5, 2916.8, 2850.3, 1738.5, 1681.6, 1600.6, 1504.2, 1466.6, 1406.8, 1349.0, 1321.0, 1308.5, 1284.4, 1224.6, 1106.0, 990.3, 964.2, 941.1, 884.2, 867.8, 721.2

Compounds (1)-1, (1)-13, and (1)-26 were all biased to a thermally stable resonance ring structure (B) as the lithium salt, however, as the sodium salt, some free body structures certainly remain. This suggests that when comparing the lithium salt and sodium salt, equilibrium is more biased to the thermally stable resonance ring structure (B) for the lithium salt than for the sodium salt, and the compound of the present invention is expected to have lithium salt separation ability of high selectivity.

Example 3

It can be seen from the following X-ray diffraction (XRD) and polarization microscope observation that (1)-13 is a liquid crystal compound representing a smectic liquid crystal phase having a layered structure.

<XRD>

The X-ray diffraction pattern of (1)-13 at 23° C. (liquid crystal state) is shown in Table 1. From the d lattice spacing ratio of 1:1/2:1/3:1/4, it was confirmed that (1)-13 has the layered structure.

TABLE 1

| peak-No. | 2θ [deg] | d [Å] | d lattice spacing ratio |
|---|---|---|---|
| 1 | 1.98 | 44 | 1 |
| 2 | 4.18 | 21 | 1/2 |
| 3 | 6.4 | 13 | 1/3 |
| 4 | 8.6 | 10 | 1/4 |

It was found that the lithium salt of (1)-13 which is (1)-13L is also a liquid crystal compound representing a smectic liquid crystal phase having a layered structure, by the following X-ray diffraction (XRD) and polarization microscope observation.

<XRD>

The X-ray diffraction pattern of (1)-13L at 23° C. (liquid crystal state) is shown in Table 2. Though it is very similar to (1)-13, since a hydrogen ion is substituted with a lithium ion, the d lattice spacing was a little larger; however, from the d lattice spacing ratio of 1:1/2:1/3:1/4, it was confirmed that (1)-13L also has the layered structure.

TABLE 2

| peak-No. | 2θ [deg] | d [Å] | d lattice spacing ratio |
|---|---|---|---|
| 1 | 1.97 | 44.9 | 1 |
| 2 | 4.13 | 21.4 | 1/2 |
| 2 | 7.02 | 12.6 | 1/3 |
| 4 | 8.42 | 10.5 | 1/4 |

Example 4

<Polarization Microscope Observation>

Figure 3:
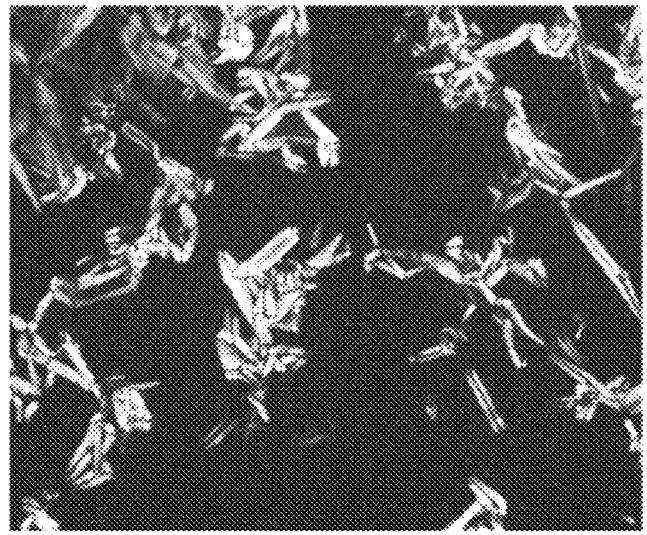
FIG. 3 is an image of a polarization microscope observation of compound (1)-13 at room temperature.

FIG. 3 is an image of polarization microscope observation of compound (1)-13 at room temperature. In a liquid crystal state (26° C.), a specific texture was observed on a smectic B phase under a Cross Nicole condition.

Figure 4:
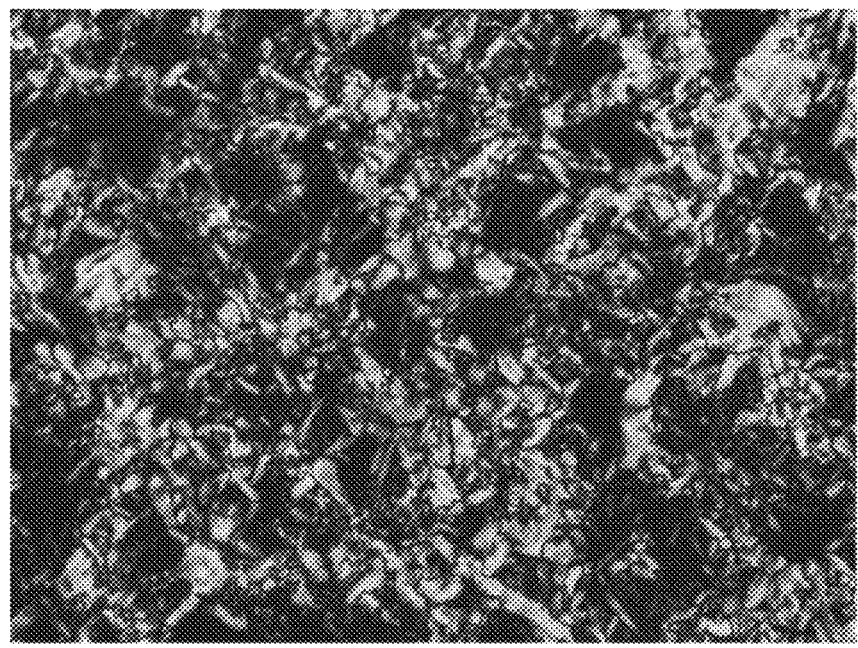
FIG. 4 is an image of a polarization microscope observation of compound (1)-26 at room temperature.

FIG. 4 is an image of polarization microscope observation of compound (1)-13L at room temperature. In a liquid crystal state (50° C.), a specific texture was observed on a smectic B phase under a Cross Nicole condition.

Example 5

<Verification of Photopolymerization Reaction by FT-IR>

It was confirmed that the lithium salt of (1)-26, (1)-26L is polymerized in a thin film state.

Figure 5:
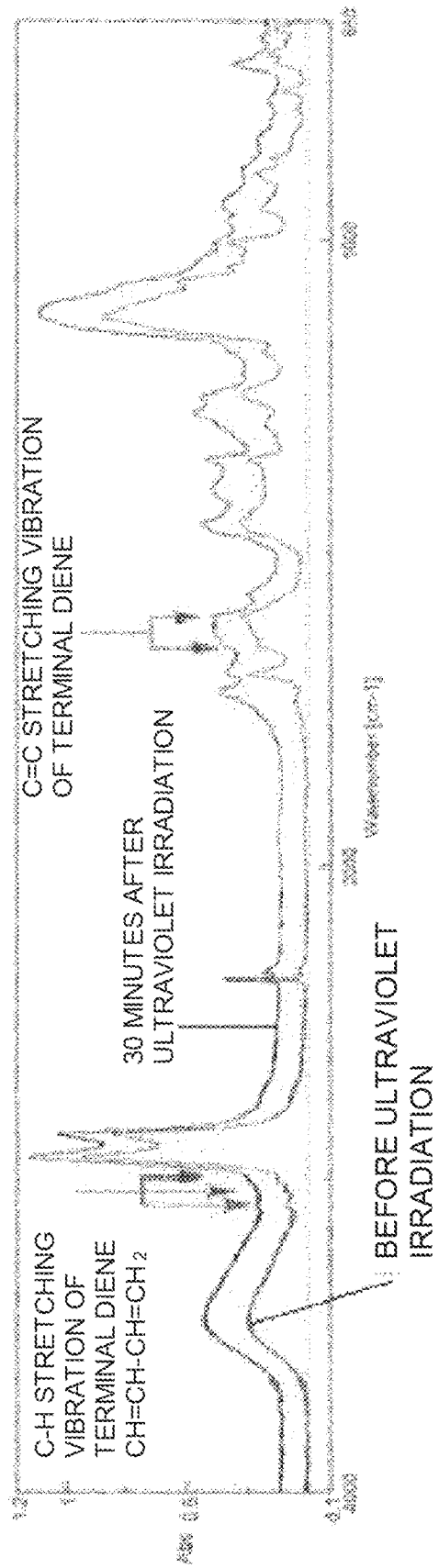
FIG. 5 is a measurement result of FT-IR before and after ultraviolet irradiation to compound (1)-26L.
Figure 6:
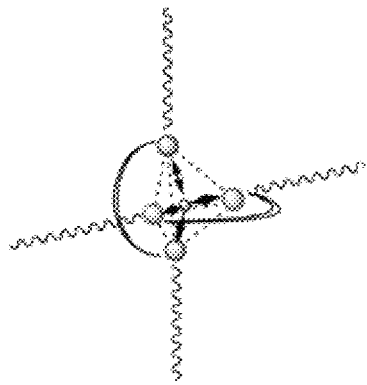
FIG. 6 is a schematic diagram of 1-position, 5-position substituent, and 3-position substituent of the acetylacetone derivative.
Figure 6:
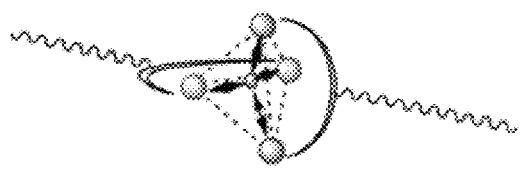
Figure 6:

A thin film having a thickness of 2 μm in which (1)-26L is mixed with 15 wt % of a photopolymerization initiator, 2,2-dimethoxy-2-phenyl acetophenone was formed on a gold-deposited substrate, irradiated with ultraviolet light for 30 minutes, and FT-IR was measured before and after irradiation. As a result, as shown in FIG. 5, C—H stretching vibration peaks at 3086.5 $cm^{-1}$, 3033.5 $cm^{-1}$, and 3003.6 $cm^{-1}$, and C═C stretching vibration peaks at 1646.9 $cm^{-1}$ and 1600.6 $cm^{-1}$ of a butanedienyl group which were present before ultraviolet light irradiation (green curve) all disappeared 30 minutes after ultraviolet light irradiation (blue curve), and thus, it was confirmed that polymerization of (1)-26L proceeded by ultraviolet light irradiation.

What is claimed is:

1. A compound represented by formula (1):

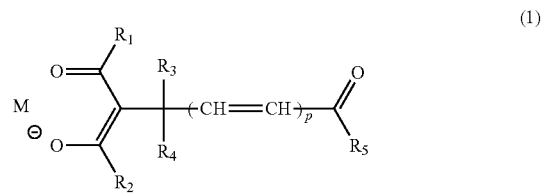

wherein
M is a hydrogen ion, or a monovalent or higher valent metal ion which may have a ligand;
$R_1$ and $R_2$ are, each independently, a substituted or unsubstituted alkyl group, alkenyl group, alkynyl group, aryl group, or heterocyclic group, and these groups may include a polymerizable group,
at least one of $R_1$ and $R_2$ is a trifluoromethyl group;
$R_3$ and $R_4$ are, each independently, a hydrogen atom, a substituted or unsubstituted alkyl group, aryl group, or heterocyclic group, and these groups include a polymerizable group;
$R_5$ is a alkyl group, alkenyl group, alkynyl group, aryl group, heterocyclic group, alkoxy group, aryloxy group, alkylamino group, or arylamino group, and these groups include a polymerizable group and may also include a substituent; and
p is 1 or 0, with a proviso that when p=0, $R_5$ is not an alkoxy group having 4 or less carbon atoms.

2. The compound according to claim 1, wherein both of $R_1$ and $R_2$ are a trifluoromethyl group.

3. The compound according to claim 1, wherein a divalent residue represented by formula (2) is included in the inside of a substituted or unsubstituted alkyl group, alkenyl group, alkynyl group, aryl group, heterocyclic group, alkoxy group, aryloxy group, alkylamino group, arylamino group, alkylthio group, or arylthio group defined as $R_5$:

wherein k is 2 or 3; and m is an integer of 1 to 20.

4. The compound according to claim 1, wherein M is a lithium ion.

5. The compound according to claim 1, wherein the compound represented by formula (1) has pKa of 3 to 6.

6. The compound according to claim 1, wherein the compound represented by formula (1) expresses liquid crystallinity.

7. A composition comprising the compound according to claim 1, wherein M is a monovalent or higher valent metal ion which may have a ligand.

8. The composition according to claim 7, wherein the composition has a cumulative structure by self-organization.

9. A composition comprising the compound according to claim 1, and a compound represented by formula (3):

wherein

R$_6$, R$_7$, and R$_8$ are, each independently, a substituted or unsubstituted alkyl group, aryl group, or heterocyclic group, which may include a polymerizable group;

any two of R$_6$, R$_7$, and R$_8$ may form a 5 to 7-membered ring containing a phosphorus atom to which the two are bonded together; or said compound may form a dimer through any one of R$_6$, R$_7$, and R$_8$; and each of R$_6$ to R$_8$ does not include a polymerizable group, or at least one of R$_6$ to R$_8$ includes a polymerizable group.

10. The composition according to claim 9, wherein at least one of the compound represented by formula (1) and the compound represented by formula (3) includes the polymerizable group, and a polymer including a repeating unit derived from the compound including the polymerizable group is included in the composition.

11. The composition according to claim 9, wherein in formula (1), M is a monovalent or higher valent metal ion which may have a ligand.

12. The composition according to claim 9, wherein the composition has a cumulative structure by self-organization.

13. A process for preparing a polymer composition, comprising: polymerizing a composition according to claim 9 comprising a compound represented by formula (1) wherein M is a monovalent or higher valent metal ion which may have a ligand, and a compound represented by formula (3), in which at least one of both compounds has a polymerizable group; eluting a metal salt thereof; and substituting M with a hydrogen atom.

14. A process for preparing a polymer composition, comprising: polymerizing a composition comprising a compound represented by formula (1) according to claim 1 wherein M is a monovalent or higher valent metal ion which may have a ligand; and at least one of R$_1$ to R$_5$ includes a polymerizable group; eluting a metal salt thereof; and substituting M with a hydrogen atom.

15. A process for preparing a compound represented by formula (1) according to claim 1, comprising reacting a compound represented by following formula (4) and a compound represented by following formula (5):

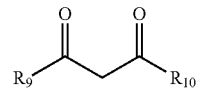

(4)

wherein R$_9$ and R$_{10}$ are a substituted or unsubstituted alkyl group, aryl group, heterocyclic group, alkenyl group or alkynyl group, which may include a polymerizable group, and at least one of R$_9$ and R$_{10}$ is a trifluoromethyl group;

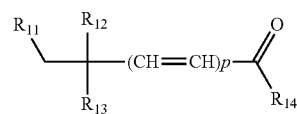

(5)

wherein R is a halogen element; R$_{12}$ and R$_{13}$ are a hydrogen atom, a substituted or unsubstituted alkyl group, aryl group, or heterocyclic group; R$_{14}$ is a substituted or unsubstituted alkyl group, alkenyl group, alkynyl group, aryl group, heterocyclic group, alkoxy group, aryloxy group, alkylamino group, or arylamino group; groups defined as R$_{12}$ to R$_{14}$ may include a polymerizable group; and p is 0 or 1, with a proviso that when p=0, R$_{14}$ is not an alkoxy group having 4 or less carbon atoms.

16. The process according to claim 15, wherein the compound represented by formula (4) and the compound represented by formula (5) are reacted in the coexistence of an iodine salt of an organic compound.

\* \* \* \* \*

UNITED STATES PATENT AND TRADEMARK OFFICE
CERTIFICATE OF CORRECTION

Page 1 of 1

PATENT NO. : 10,835,895 B2
APPLICATION NO. : 16/090405
DATED : November 17, 2020
INVENTOR(S) : Takashi Kato It is certified that error appears in the above-identified patent and that said Letters Patent is hereby corrected as shown below:

In the Claims

Column 38, Line 25, Claim 15, delete "R" and insert --$R_{11}$--.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*